United States Patent [19]
Jang

[11] Patent Number: 5,554,118
[45] Date of Patent: *Sep. 10, 1996

[54] UNIVERSAL MODE VASCULAR CATHETER SYSTEM

[76] Inventor: G. David Jang, 636 Golden West Dr., Redlands, Calif. 92373

[*] Notice: The term of this patent shall not extend beyond the expiration date of Pat. No. 5,395,335.

[21] Appl. No.: 172,640

[22] Filed: Dec. 22, 1993

Related U.S. Application Data

[63] Continuation-in-part of Ser. No. 756,295, Sep. 6, 1991, abandoned, Ser. No. 705,295, May 24, 1991, and Ser. No. 714,642, Jun. 13, 1991.

[51] Int. Cl.$^6$ .................................................. A61M 29/00
[52] U.S. Cl. ........................... 604/96; 604/102; 604/164; 604/283; 606/194
[58] Field of Search .................. 604/95, 96, 160–161, 604/165, 263, 280–284, 102, 164; 606/194; 128/772, 656–658

[56] References Cited

U.S. PATENT DOCUMENTS

| | | |
|---|---|---|
| Re. 31,855 | 3/1985 | Osborne. |
| 3,262,449 | 8/1966 | Pannier et al. . |
| 3,297,030 | 1/1967 | Czorny et al. . |
| 3,550,591 | 12/1970 | MacGregor. |
| 3,682,173 | 8/1972 | Center. |
| 3,853,130 | 12/1974 | Sheridan. |
| 4,037,599 | 7/1977 | Raulerson. |
| 4,054,136 | 10/1977 | von Zeppelin. |
| 4,079,738 | 3/1978 | Dunn et al. . |
| 4,175,564 | 11/1979 | Kwak. |
| 4,411,055 | 10/1983 | Simpson et al. . |
| 4,411,654 | 10/1983 | Boarini et al. . |
| 4,569,347 | 2/1986 | Frisbie. |
| 4,573,470 | 3/1986 | Samson et al. . |
| 4,581,017 | 4/1986 | Sahota. |
| 4,585,013 | 4/1986 | Harris. |
| 4,596,559 | 6/1986 | Fleischacker. |
| 4,619,644 | 10/1986 | Scott. |
| 4,631,056 | 12/1986 | Dye. |
| 4,631,059 | 12/1986 | Wolvek et al. . |
| 4,723,948 | 2/1988 | Clark et al. . |
| 4,747,833 | 3/1988 | Kousai et al. . |
| 4,748,982 | 6/1988 | Horzewski et al. . |
| 4,762,129 | 8/1988 | Bonzel. |
| 4,771,777 | 9/1988 | Horzewski et al. . |
| 4,813,930 | 3/1989 | Elliott. |
| 4,883,468 | 11/1989 | Kousai et al. . |
| 4,888,000 | 12/1989 | McQuiklen et al. . |
| 4,931,049 | 6/1990 | Klimas. |
| 4,947,864 | 8/1990 | Shokey et al. . |
| 4,988,356 | 1/1991 | Crittenden et al. . |
| 4,997,424 | 3/1991 | Little. |
| 5,102,403 | 4/1992 | Alt. |
| 5,135,535 | 8/1992 | Kramer. |
| 5,154,725 | 10/1992 | Leopold. |
| 5,171,222 | 12/1992 | Eutenever et al. . |
| 5,195,978 | 3/1993 | Schiffer. |
| 5,205,822 | 4/1993 | Johnson et al. . |

FOREIGN PATENT DOCUMENTS

| | | |
|---|---|---|
| 3934695 | 4/1991 | Germany. |

*Primary Examiner*—John D. Yasko
*Assistant Examiner*—Mark Bockelman

[57] ABSTRACT

A multi-lumen vascular catheter for use with a guidewire, comprising a longitudinally extending catheter shaft having a proximal end and a distal end and having at least first and second lumens extending distally from the proximal end, each of the lumens having a proximal opening, wherein the first lumen is adapted to receive a guidewire, and a first connector at the proximal end of the catheter providing a first channel communicating with the interior of the first lumen for insertion of a guidewire therethrough, the connector including means for permitting a guidewire extending longitudinally through the first channel into the first lumen to be moved laterally out of the first channel through the first connector beginning at the proximal end of the first connector. The catheter may be an angioplasty catheter. Also disclosed are methods for using the catheter and for exchanging catheters and guidewires during vascular catheterization procedures.

44 Claims, 27 Drawing Sheets

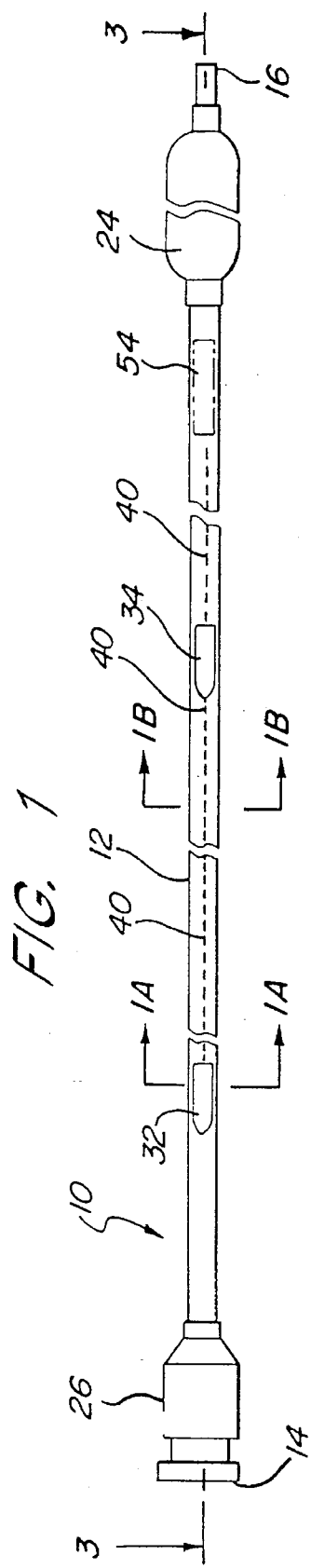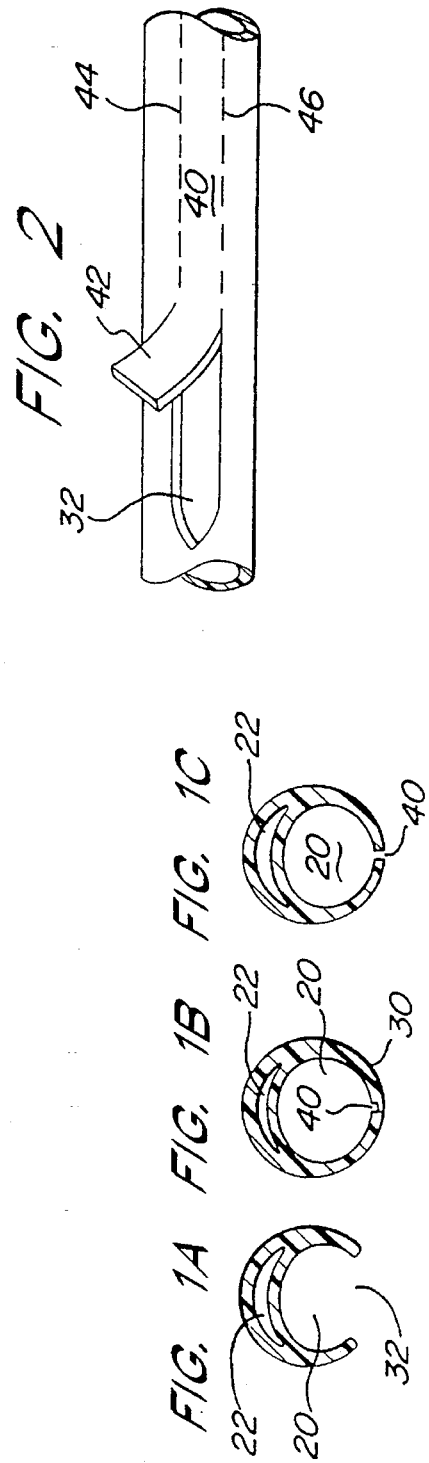

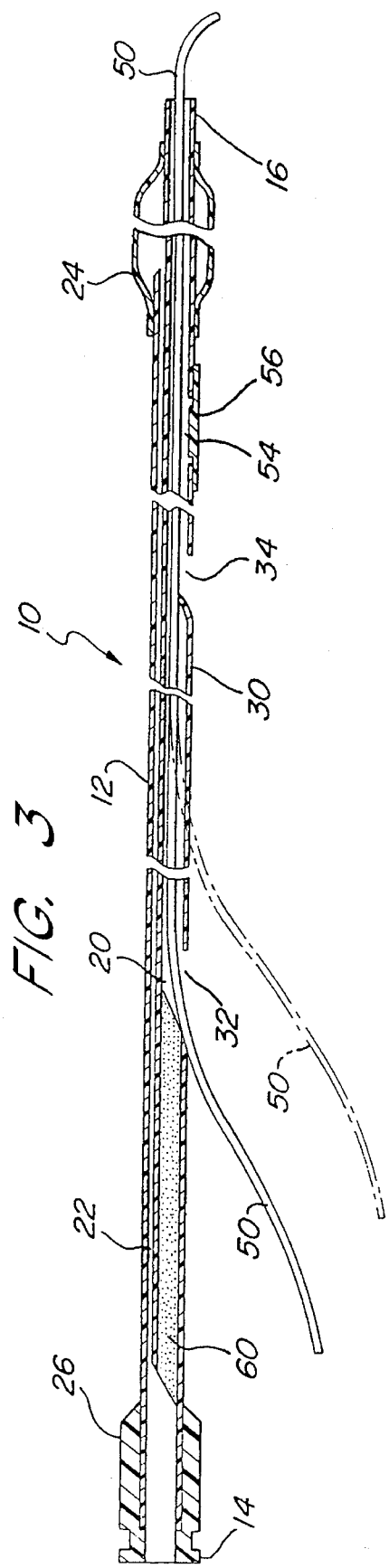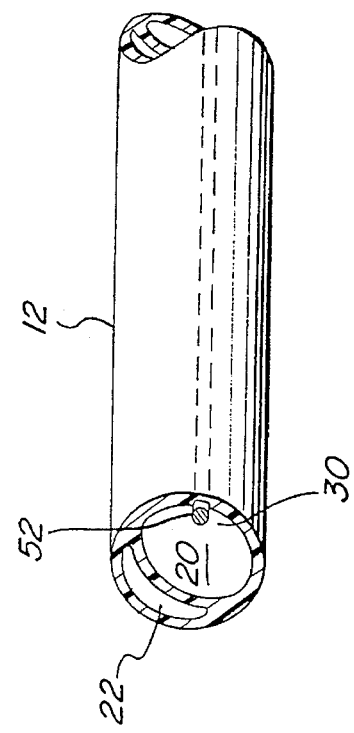

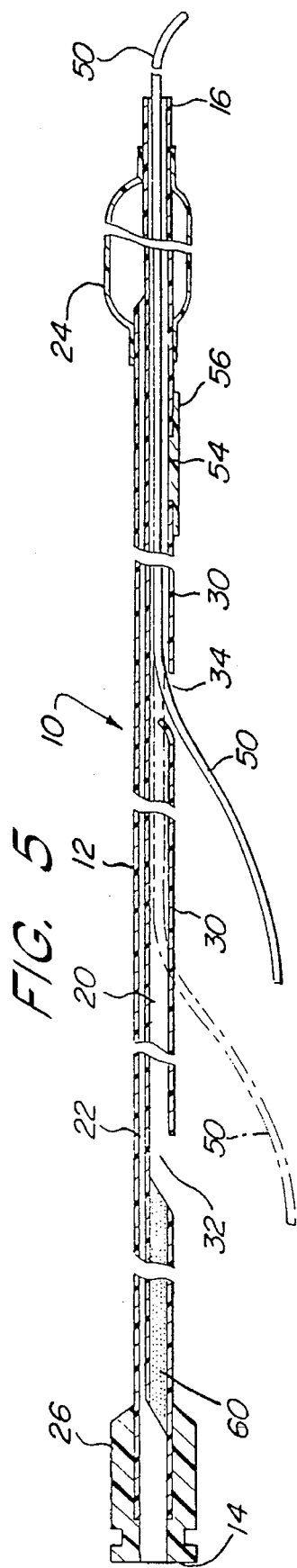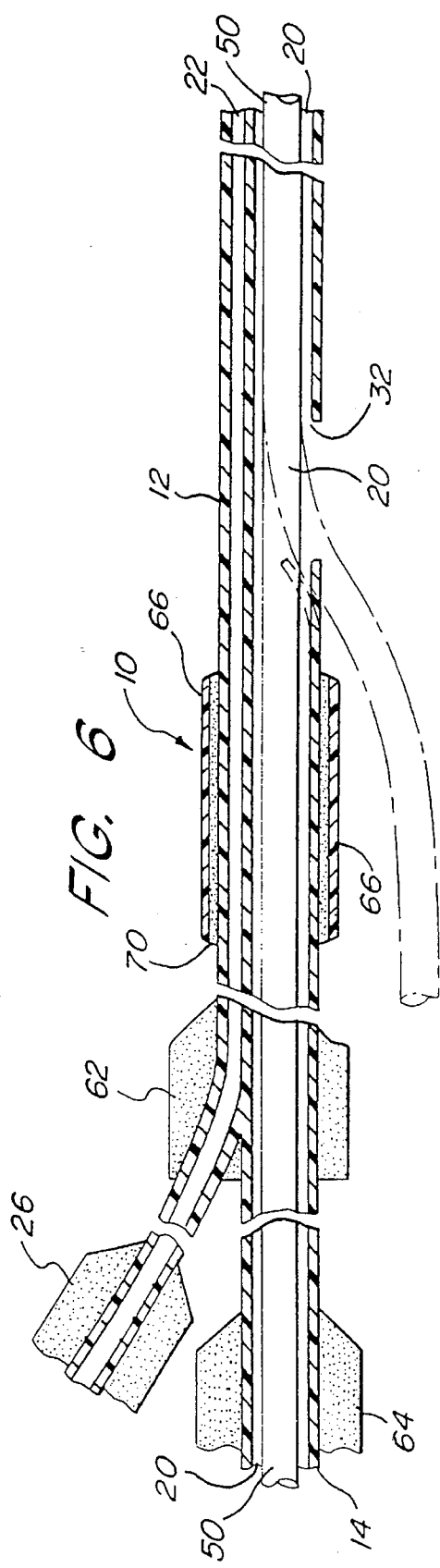

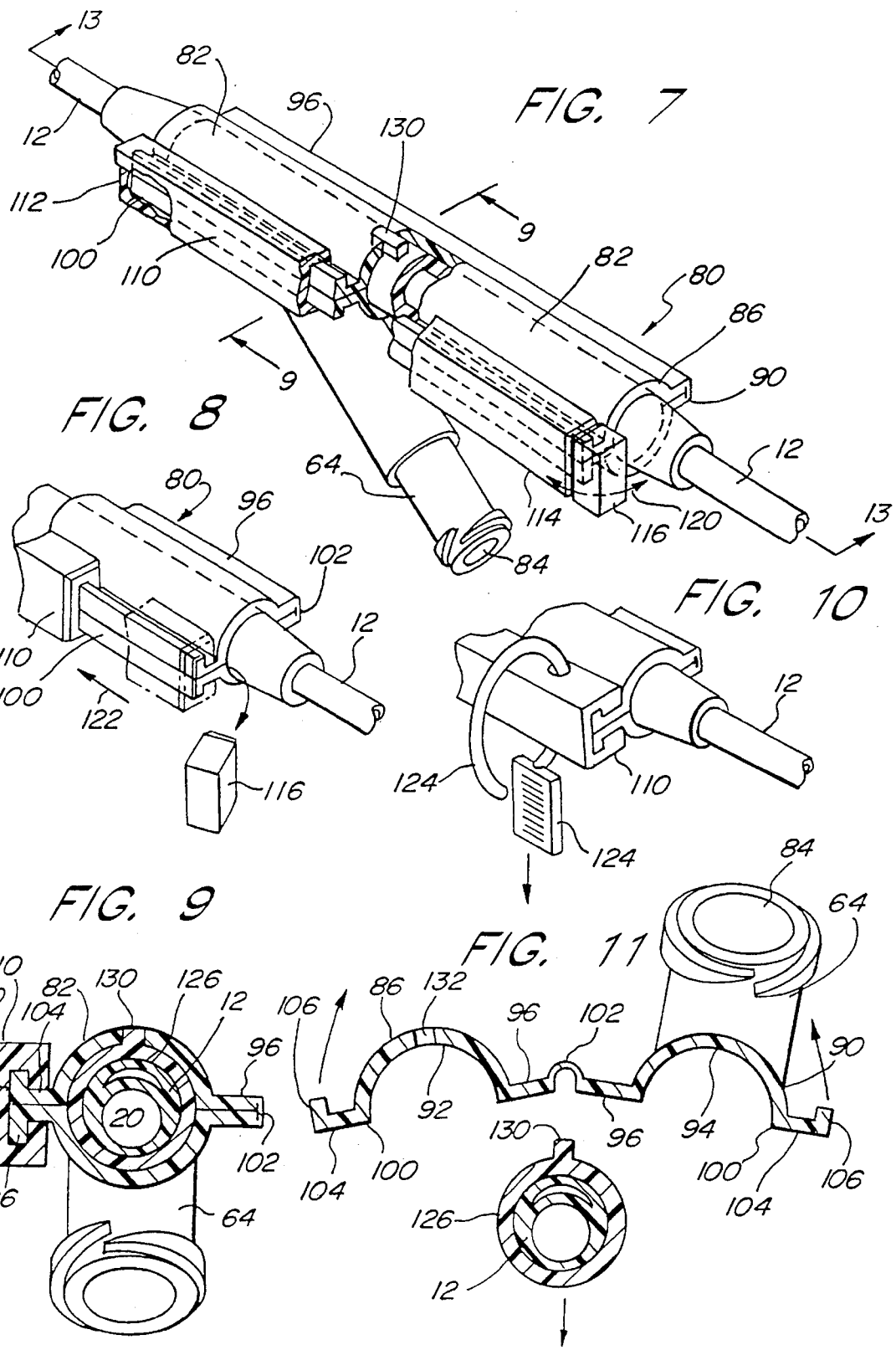

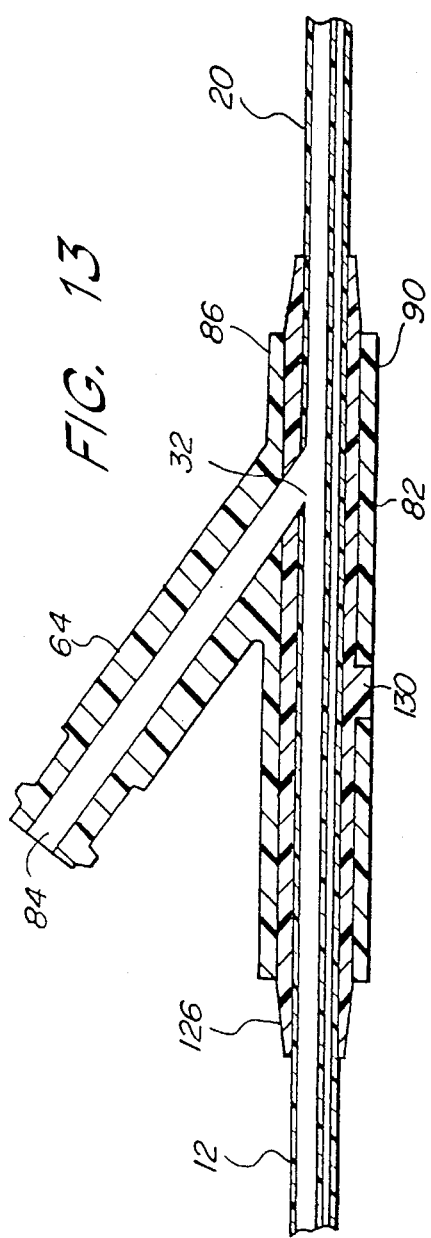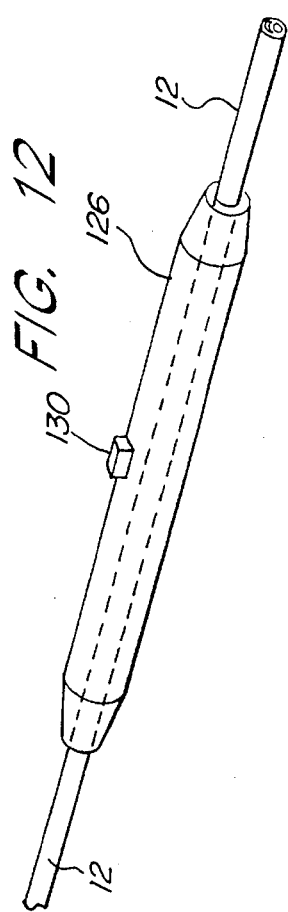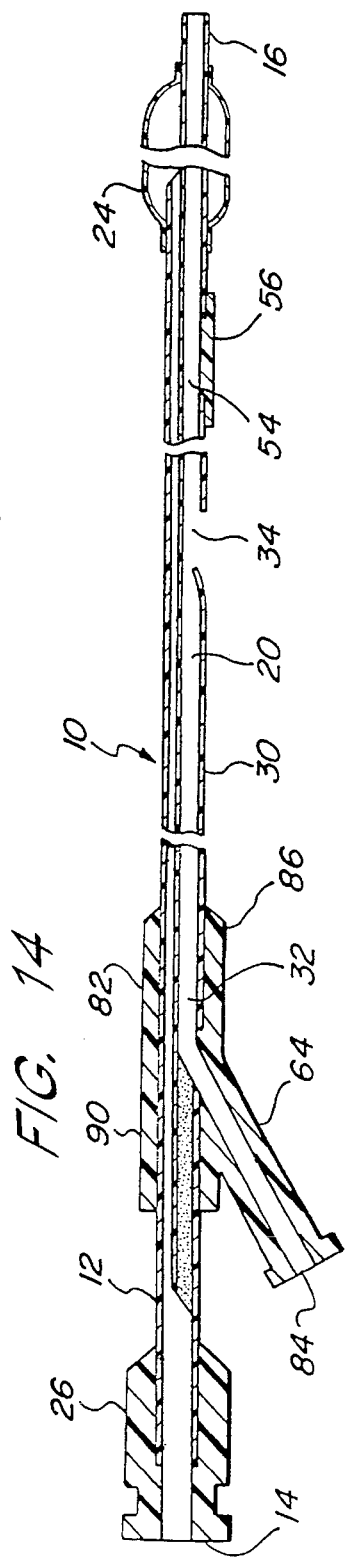

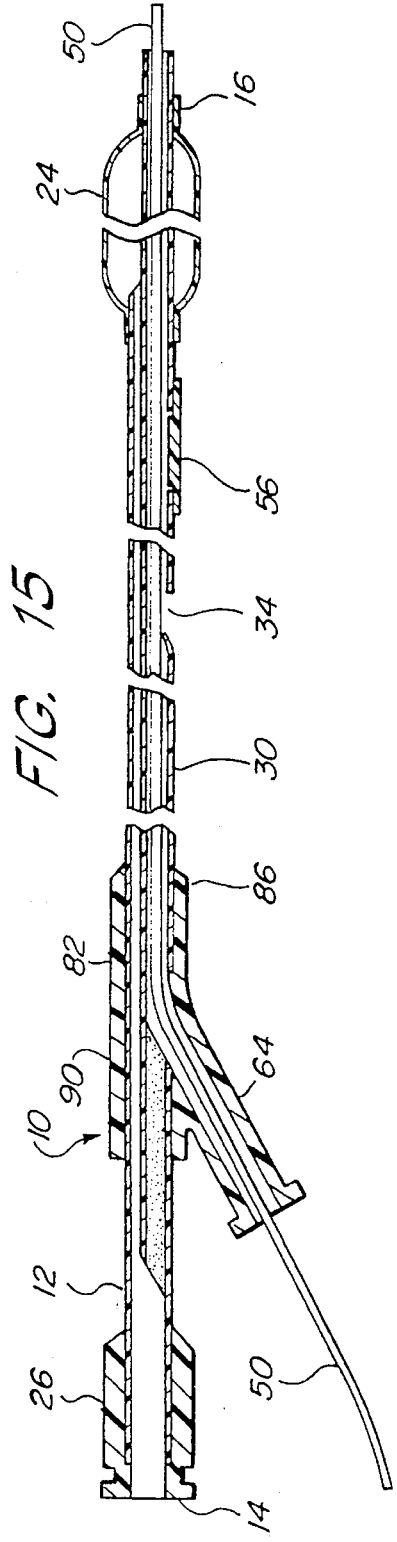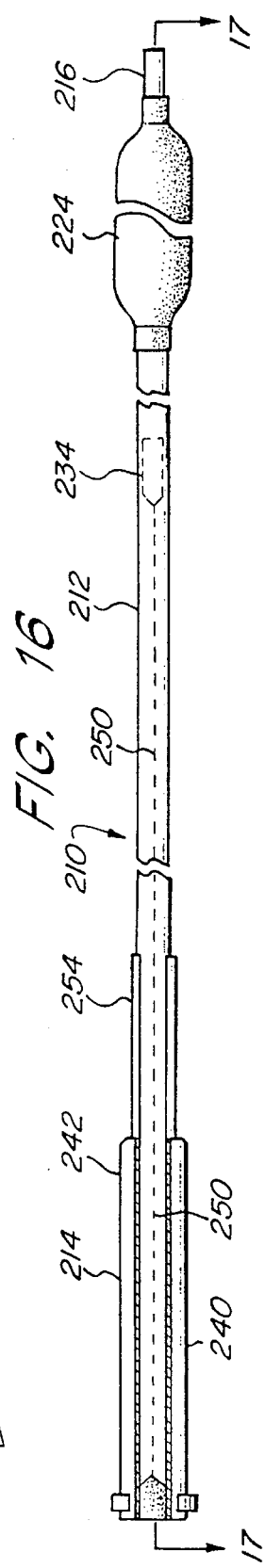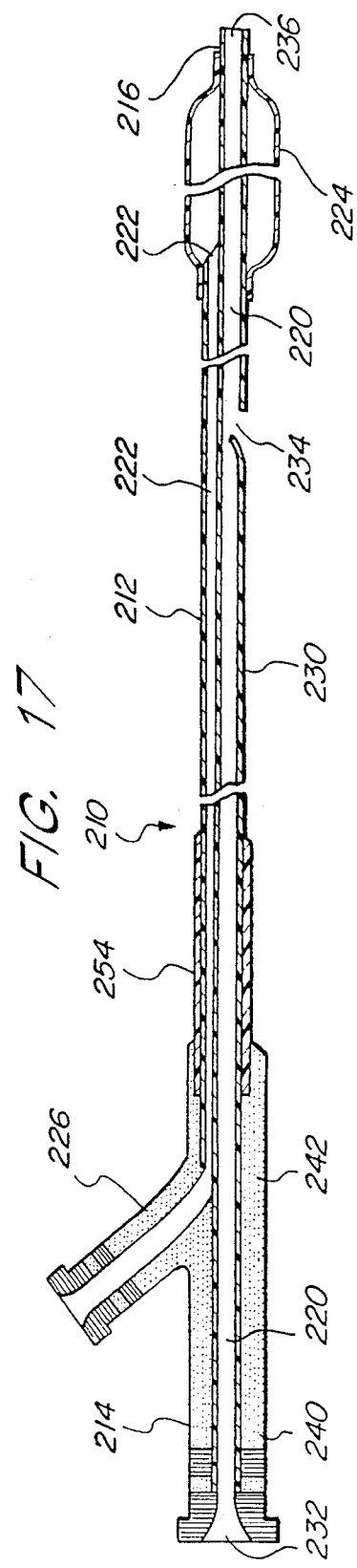

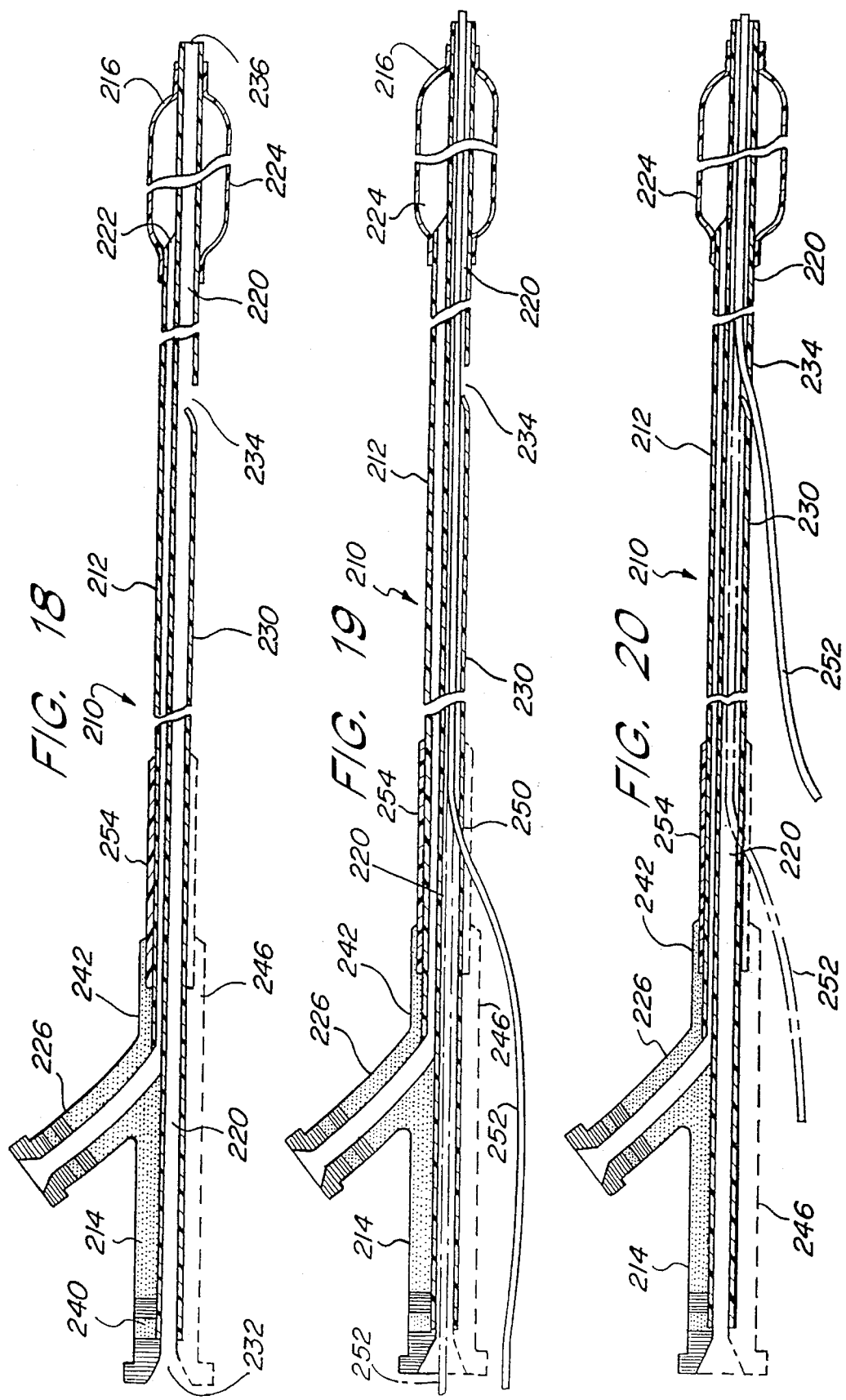

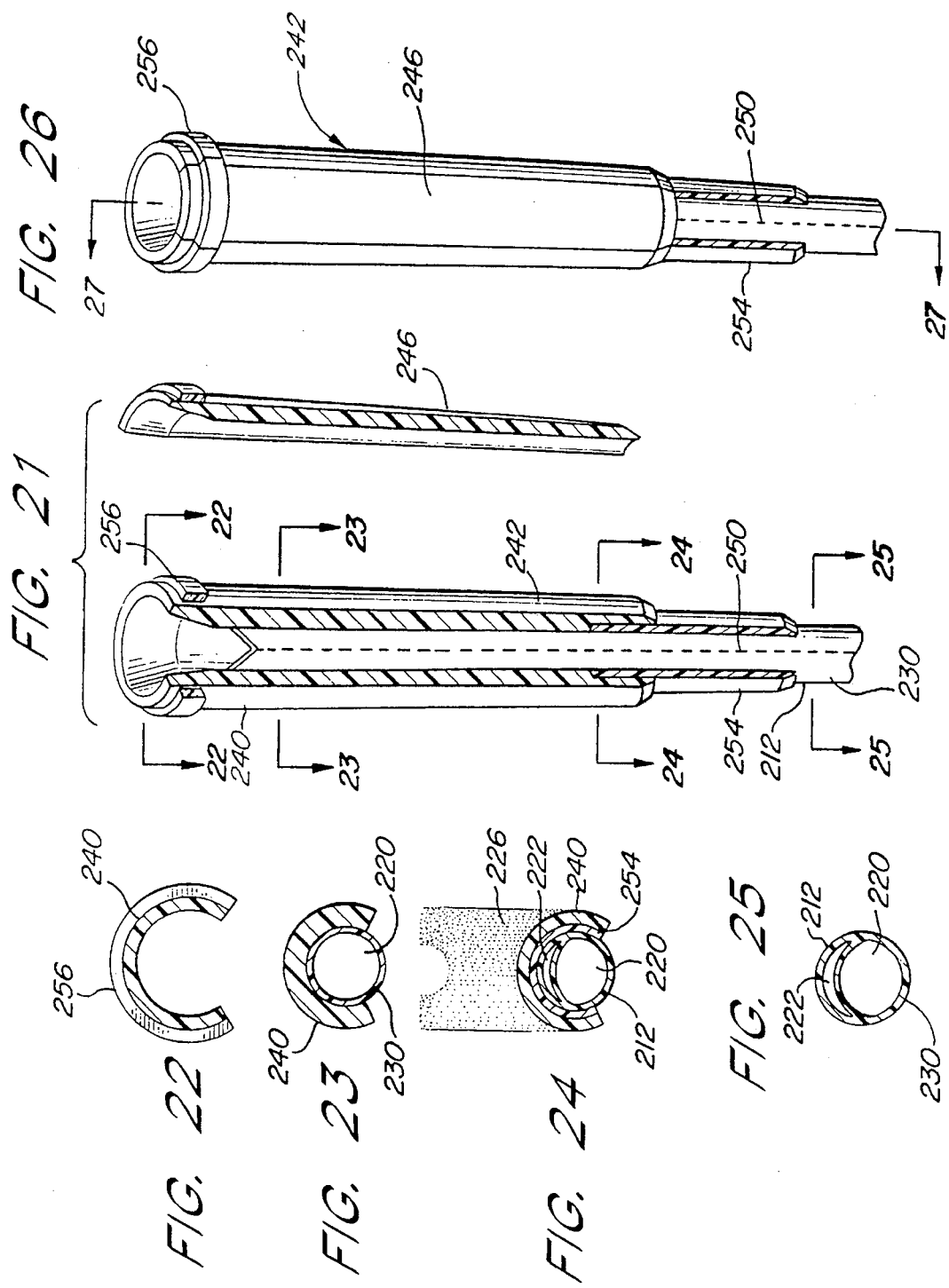

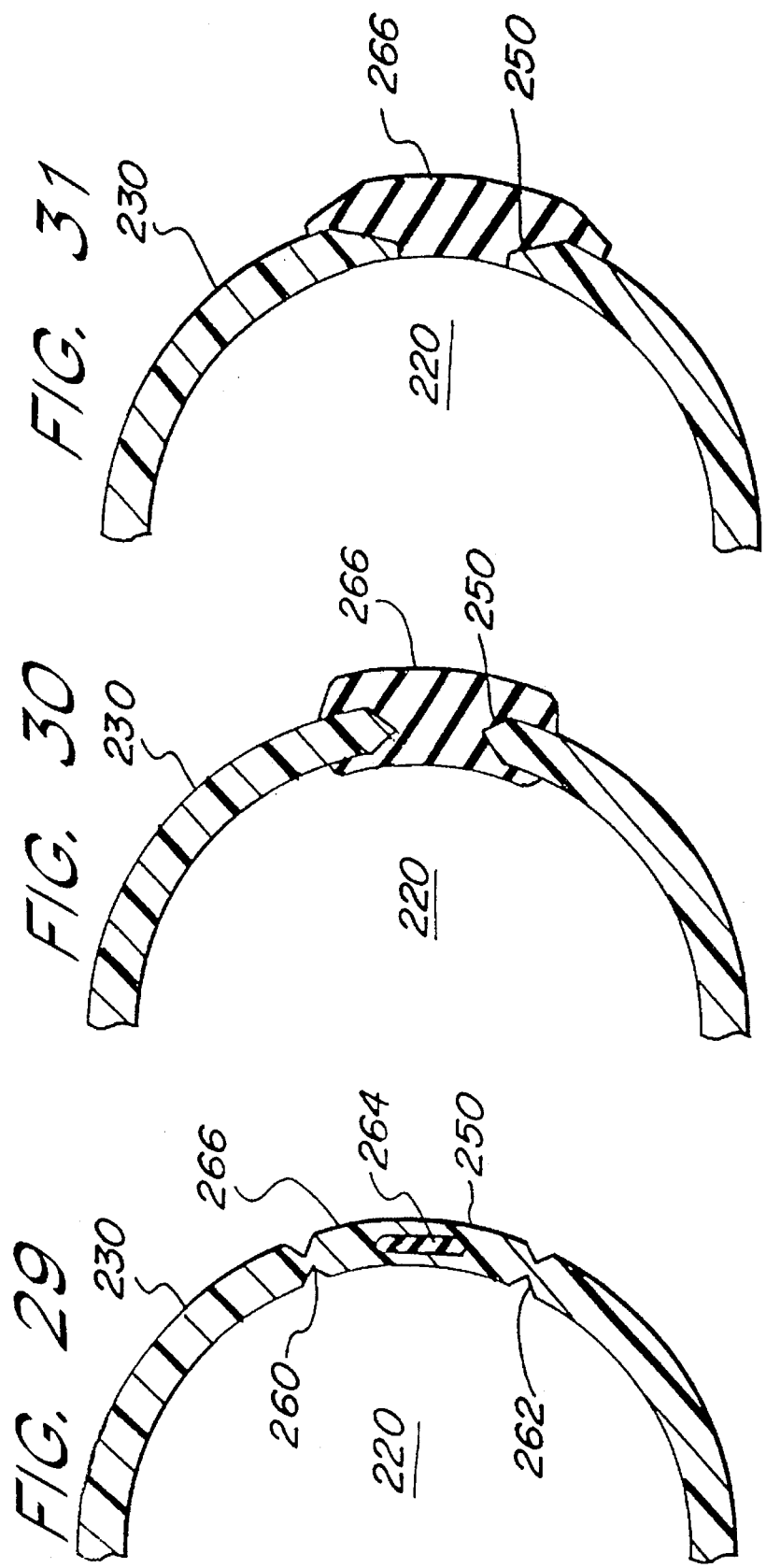

UNIVERSAL MODE VASCULAR CATHETER SYSTEM

CROSS REFERENCE TO RELATED APPLICATIONS

This application is a continuation in part of U.S. application Ser. No. 07/756,295, filed Sep. 6, 1991 now abandoned, U.S. patent application Ser. No. 07/705,295, filed May 24, 1991 pending, and U.S. application Ser. No. 07/714,642, filed Jun. 13, 1991 pending, the disclosures of which are hereby incorporated by reference.

FIELD OF THE INVENTION

This invention relates to vascular catheters (such as angioplasty catheters) specially adapted for rapid exchange of both the guidewire and the catheter during use. It also relates to the method of using those catheters.

BACKGROUND OF THE INVENTION

Percutaneous transluminal coronary angioplasty (PTCA) has emerged as the major viable present alternative to bypass surgery for revascularization of stenotic and occluded coronary arteries. Although transluminal angioplasty has application in peripheral artery disease, it is most widely used in the treatment of coronary artery disease. Unlike bypass surgery, percutaneous angioplasty does not require general anesthesia, cutting of the chest wall, extracorporeal perfusion, or transfusion of blood. Percutaneous coronary angioplasty is not only less invasive and less traumatic to the patient, it is also less expensive because the angioplasty patient will have a shorter hospital stay and shorter post-procedure recovery time.

Percutaneous transluminal angioplasty is performed by making a skin puncture with a specially-designed needle in one of the groins, and then introducing a guiding catheter (typically 8 or 9 French size) into the aorta and coronary artery orifice. A smaller caliber catheter which has a built-in inflatable and deflatable balloon of predetermined size and diameter is passed through the guiding catheter which is positioned in the opening of a target artery. This balloon catheter (with the balloon totally deflated by negative pressure) is advanced inside the target artery toward the point of obstruction that needs to be dilated. The guidewire plays an essential role in leading the balloon catheter to the target coronary artery in safety and non-traumatic fashion. With the balloon portion of the catheter properly positioned inside the obstructed segment of the artery, under X-ray fluoroscopic observation, the balloon is inflated by injecting contrast media mixed with saline at a pressure sufficient to overcome the resistance of the arteriosclerotic plaque of the obstructed segment.

By inflating the balloon in the stenosis multiple times over a period of between 10–30 seconds and one or two minutes (allowing blood flow between inflations), the desired dilation of the obstructed segment of the artery can be achieved. When the desired results have been obtained by balloon inflations, the guiding catheter, the balloon catheter (with the balloon completely deflated with negative pressure) and the guidewire are withdrawn from the artery and the patient and the procedure is successfully terminated.

The size and diameter of the balloon to be used in a transluminal angioplasty should be approximately matched to the size and native diameter of the obstructed segment of the artery to be dilated. If the balloon size and diameter is smaller than the native artery, the results of balloon angioplasty are suboptimal, requiring a second dilation with a larger-sized balloon, and if balloon size is too large for the native artery, complications may occur due to arterial wall damage.

During the angioplasty procedure, a guidewire is first advanced into the desired location, after which the angioplasty catheter is advanced over the guidewire. It is sometimes necessary to replace (or exchange) either the guidewire or the balloon catheter during the procedure.

If the balloon is undersized, for example, the catheter must be withdrawn and replaced with a larger balloon catheter in order to permit adequate dilatation of the lesion. With conventional over-the-wire catheters, in which the guidewire lumen extends the entire length of the catheter shaft, a guidewire extension (e.g., 145 cm long) must first be attached to the regular guidewire (e.g. 175 cm long) being used outside the patient before the catheter is withdrawn. This permits the distal end of guidewire to be held in position while the catheter is removed and a new catheter is exchanged. Usually, two to three operators are needed to effect such a catheter exchange.

The catheter disclosed in U.S. Pat. No. 4,762,169 avoids the necessity for extending the guidewire or exchange guidewire (e.g. 300 cm in length) by having a short guidewire lumen that extends substantially only through the distal end of the catheter. This type of catheter is referred to herein as a rapid-exchange catheter. Thus, the guidewire is outside the catheter shaft for much of the catheter length, and is inside the catheter at only the distal end. The catheter can be exchanged without extending the 175 cm regular guidewire, and the exchange can be effected by one or two operators. However, this catheter has a serious drawback of not being able to permit ready exchange of guidewires. In clinical practice, the need for guidewire exchange is more common.

Conventional over-the-wire angioplasty catheters, with a guidewire lumen extending their entire length, permit simple guidewire exchange. During angioplasty procedures, the guidewire tip may become damaged, may be needed of a different type of guidewire or may need to be reshaped to complement the patient's vasculature. The guidewire exchange procedure is readily accomplished with such a conventional over-the-wire catheter. However, with the rapid-exchange type catheter of U.S. Pat. No. 4,762,129, guidewire exchange requires complete removal and reinsertion of both the guidewire and the angioplasty catheter; thus, defeating the original goal of expedient advantage of the rapid-exchange catheter.

Another disadvantage of the rapid-exchange catheter is back bleeding. While the guidewire is being manipulated to select the target vessel or to cross the culprit lesion, the Tuehy-Borst adapter must be loosened. This, in turn, permits backbleeding to occur.

Accordingly, there is a need for an angioplasty catheter that permits rapid-exchange of both the catheter and the guidewire. There is also a need for a catheter that will permit the user to select the mode of usage between the rapid-exchange and the over-the-wire systems.

SUMMARY OF THE INVENTION

In accordance with a first aspect of the present invention, there is provided a multi-lumen vascular catheter adapted for use with a guidewire, comprising a longitudinally extending catheter shaft adapted for use within the vasculature of a patient having a proximal end and a distal end and having at least a first and a second lumen extending distally from the proximal end, each of the lumens having a proximal opening (preferably at or adjacent to the proximal end), wherein the first lumen is adapted to receive a guidewire, the first lumen further comprising guidewire removing means extending distally from the proximal opening, and a first connector at or near the proximal end of the catheter, the connector encircling the catheter shaft and providing a first port communicating with a first channel, the first channel being in communication with the interior of the first lumen and being adapted for insertion of a guidewire therethrough, the connector including means for permitting the connector to be separated longitudinally and a portion thereof to be moved laterally away from the catheter shaft, such that a guidewire extending longitudinally through the first channel into the first lumen may be moved laterally out of the first channel of the connector and out of the first lumen through the guidewire removing means. Preferably, the first connector is adapted to separate into first and second parts to permit the lateral movement of a guidewire out of the first channel through the first connector. The catheter may additionally comprise a second connector at the proximal end of the catheter providing a second channel communicating with the interior of the second lumen. Such second connector may be located proximally or distally of the first connector. In a preferred embodiment, the first and second connectors are joined together in the form of a "Y". In a highly preferred embodiment, the catheter further includes guidewire removing means in the outside wall of the first lumen extending distally from the proximal opening adapted for permitting a guidewire when extending through the first lumen to be moved laterally from the first lumen through the outside wall of the guidewire lumen. In one embodiment, the guidewire removing means is a slit. Preferably, the guidewire removing means is continuous from the proximal opening to a point at least 40 cm from the proximal end. Alternatively, the guidewire removing means is discontinuous, forming a perforated line from the proximal opening to a point at least 40 cm from the proximal end. Alternatively, the guidewire removing means may be a weakened area of the wall of the first lumen adapted to be severed for removal of the guidewire therethrough. Preferably, the weakened area comprises a pair of juxtaposed grooves, one on the inside and the other on the outside of the wall of the first lumen. Also, the guidewire removing means can be a portion of the outside wall of the first lumen adapted to be removed from the catheter shaft in the form of a strip. In another highly preferred embodiment, the catheter further comprises a permanently formed side port located within about 80 cm of the distal end, the side port extending through the outside wall of the first lumen and adapted to permit insertion of a guidewire therethrough. Preferably, the guidewire removing means extends from the proximal end of the catheter shaft to point proximal of the side port. In a highly preferred embodiment, the distance of such point is between about 0.1 cm and 40 cm proximal of the side port. Preferably, the side port can be constructed to permit a guidewire to pass through the side port and through the portion of the first lumen distal to the side port, but is adapted to prevent a guidewire in the portion of the first lumen proximal to the side port from passing out of the lumen through the side port. In a highly preferred embodiment, the catheter further comprises an angioplasty balloon located at the distal end of the catheter, the interior of the balloon in fluid communication with the second lumen.

In accordance with another aspect of the present invention, there is provided an angioplasty balloon catheter comprising a catheter shaft adapted for use within the vasculature of a patient having a proximal end and a distal end, an inflatable balloon at or near the distal end, a balloon inflation lumen extending through the shaft and in communication with the balloon, a guidewire lumen extending through the shaft adapted for receiving a steerable guidewire, wherein the guidewire lumen has an outside wall, and a proximal opening at or near the proximal end of the shaft adapted for insertion of a guidewire into the lumen, and means formed in the outside wall of the guidewire lumen extending distally from the proximal opening to a point at least 40 cm from the proximal end adapted for permitting a guidewire in the guidewire lumen to be moved laterally from the guidewire lumen through the outside wall of the guidewire lumen, provided that the means is not a fully formed slit prior to the removal of a guidewire therethrough. In a highly preferred embodiment, the catheter further comprises a side port through the outside wall of the guidewire lumen adapted for passage of a guidewire into the lumen through the side of the catheter shaft, the side port located distally of the proximal opening and within about 80 cm of the balloon. Preferably, the guidewire removing means extends to a point proximal of the side port. In a highly preferred embodiment, the point is between about 0.1, 0.5, 1, 2, 5, or 10 cm and 20, 30, 40, 50, or 60 cm proximal of the side port. The side port itself is preferably located proximal of the balloon and at least 5 cm, 10 cm, 15 cm, 20 cm, or 25 cm proximally of the distal end of the catheter. The guidewire removing means may be a discontinuous slit, forming a perforated line from the proximal opening to the side port. Alternatively, the guidewire removing means may be a weakened area of the wall of the guidewire lumen adapted to be severed for removal of a guidewire therethrough. In a preferred embodiment, the catheter may further comprise a second side port distal to the first side port communicating with the interior of the guidewire lumen. In another preferred embodiment, the proximal opening is formed in the side of the catheter at a point distal of the proximal end of the catheter, further comprising a guidewire adapter at the proximal end of the catheter communicating with the guidewire lumen, so that a guidewire can be inserted into the guidewire lumen at the proximal portion of the catheter either through the guidewire adapter or through the proximal opening.

In accordance with another embodiment of the invention, there is provided an angioplasty balloon catheter adapted for vascular use, comprising a catheter shaft with a proximal end and a distal end and having a first lumen extending therethrough, the first lumen having an outside wall and being adapted to receive a guidewire extending through the first lumen, and an inflatable balloon at or near the distal end, a balloon inflation lumen extending through the shaft and in communication with the balloon, a guidewire connector attached to the proximal end of the catheter communicating with the first lumen and adapted to direct a guidewire into the first lumen, the connector further having a wall, and means for permitting a guidewire, when extending through the first lumen, to be removed laterally through the wall of the connector and the outside wall of the first lumen while maintaining the longitudinal positioning of a guidewire in a patient, provided that the means is not a fully formed slit prior to the removal of a guidewire therethrough. In a preferred embodiment, the guidewire connector is adapted to be removed, at least in part, from the catheter shaft. In another preferred embodiment, the guidewire connector comprises a first portion is adapted to be laterally removed away from the first lumen and a second portion that is adapted to remain on the catheter shaft.

In accordance with another embodiment of the present invention, there is provided an angioplasty catheter for use in an animal body with a guidewire, comprising a catheter shaft having a proximal end and a distal end with at least two lumens extending therethrough, and a "Y" connector surrounding at least a portion of the proximal end of the catheter shaft and having at least two arms, one arm providing an access channel into one of the lumens and another arm providing an access channel into another of the lumens, wherein the "Y" connector has at least two segments joined together in a separable manner along a longitudinal line that runs generally in the direction of one of the access channels so that upon separation of the segments, the "Y" connector no longer surrounds at least one of the access channels in the portion of the proximal end of the catheter shaft. In a preferred embodiment, upon separation of the segments, one of the segments is completely removable from the catheter shaft.

In accordance with another embodiment of the present invention, there is provided an angioplasty catheter that is convertible to and from over-the-wire mode to rapid-exchange mode, comprising a catheter shaft with a proximal opening in a proximal end and a distal opening in a distal end and having a first lumen extending therethrough, the first lumen having an outside wall and being adapted to receive a guidewire extending through the first lumen and guidewire removing means formed in the outside wall of the first lumen, the guidewire removing means being adapted to allow a guidewire extending through the first lumen to be removed laterally through the outside wall and a permanently formed side port located within about 80 cm of the distal end, the side port extending through the outside wall of the first lumen and adapted to permit insertion of a guidewire therethrough and, wherein the guidewire removing means terminates a point proximal of the side port, an inflatable balloon mounted at or near the distal end of the catheter shaft in communication with a balloon inflation lumen extending through the shaft, a dual arm connector mounted at or near the proximal end of the shaft, the connector having first and second arms, the first arm forming a first channel encircling the catheter shaft and having an outside wall and a proximal opening and being in communication with the first lumen, the first channel being adapted to receive a guidewire extending through the proximal opening of the first channel and into the first lumen of the catheter, and the second arm forming a second channel having an outside wall and a proximal opening in communication with the balloon inflation lumen, the connector housing further comprising a removable wall section having a width in the outside wall of the first channel that is reversibly and completely disengageable from the connector housing, wherein, the width of the removable wall section is sufficient to permit a guidewire extending through the first channel to be laterally removed from the first channel, and, wherein, upon disengagement of the removable wall section the catheter is no longer encircled by the connector housing and so as to expose the guidewire removing means in the catheter shaft and a guidewire extending from the proximal opening of the first channel and into the first lumen can be removed laterally out of the connector and out of the catheter through the guidewire removing means, and means disengageably mounted on the connector housing to prevent disengagement of the removable wall section, the means being further operable to reengage the removable wall section, following disengagement. In a preferred embodiment, the first channel has a circumference and the removable wall section comprises a circumferential sector large enough to allow removal of a guidewire therethrough upon detachment of the removable wall section. Preferably, the circumferential sector comprises an angle between 15 and 180 degrees of the circumference of the first channel. In highly preferred embodiments, the means comprise a detachable ring, a detachable ring mounted on a proximal end of the first channel, a system where the proximal end of the first channel additionally comprises threading and the detachable ring is secured thereon, and longitudinal slots constructed in the first channel adapted to receive the removable wall section. In a preferred embodiment, the termination point of the guidewire removing means is between about 0.1 cm and 10, 15, 20, 35, 30, 40, or 60 cm proximal of the side port.

In accordance with another preferred embodiment of the present invention, there is provided a "Y" connector, comprising a connector body having a proximal end and a distal end and having a wall with a first side and a second side, the connector body comprising a first channel extending from the proximal end to the distal end with a longitudinal section of the wall in the first side being completely removable, the connector body further comprising a second channel formed in the second side of the connector body in communication with the first channel, and wherein the distal end of the first channel of the connector body is adapted to be mounted on a catheter shaft having a first and second lumen and the proximal end of the first channel is adapted to direct a guidewire into the first lumen of the catheter and the second channel is in communication with the second lumen of the catheter.

In accordance with another preferred embodiment of the invention, there is provided a method for converting to and from over-the-wire mode to rapid exchange mode in an intravascular procedure in a patient, comprising providing the convertible catheter described above in the vasculature of a patient in over-the-wire mode with a guidewire having a proximal and distal end extending through the first channel of the connector and through the catheter shaft with the distal end of the guidewire extending from the distal end of the catheter, actuating the means for detaching and detaching the removable wall section in the first channel, removing the guidewire from the first channel and out of the catheter shaft through the guidewire removing means to the termination point of the guidewire removing means, sliding the catheter off of the guidewire, inserting proximal end of the guidewire into the distal end of the same catheter or a second catheter similar catheter and through the guidewire lumen and out through the side port in rapid-exchange mode, advancing the catheter to a position near the distal end of the guidewire, withdrawing the guidewire from the vasculature, and inserting the same or a similar guidewire into the proximal end of the catheter through the first channel of the connector, through the guidewire lumen, and out the distal end of the catheter in over-the-wire mode.

BRIEF DESCRIPTION OF THE DRAWINGS

FIG. 1 is a foreshortened plan view of a catheter according to the present invention.

FIG. 1A is a transverse cross section of the catheter of FIG. 1, taken along the line A—A.

FIG. 1B is a transverse cross section of the catheter of FIG. 1, taken along the line B—B.

FIG. 1C is a transverse cross section of the catheter of FIG. 1 corresponding to FIG. 1B, but illustrating the opening of the guidewire removing means.

FIG. 2 is a fragmentary view of a portion of the catheter shaft of the FIG. 1 catheter surrounding the proximal opening, illustrating one variation of the guidewire removing means.

FIG. 3 is a longitudinal cross section of the catheter of FIG. 1 taken along the line 3—3, illustrating the guidewire in place and the function of the guidewire removing means.

FIG. 4 is a cross sectional fragmentary perspective view of the catheter of FIG. 1, taken along the line B—B, illustrating another variation of the guidewire removing means.

FIG. 5 is a longitudinal cross section corresponding to FIG. 3, illustrating movement of the guidewire laterally out of the guidewire removing means.

FIG. 6 is a foreshortened longitudinal cross section of the proximal end of one embodiment of the catheter of the present invention.

FIG. 7 is a perspective view of a removable "Y" connector at the proximal end of the catheter shaft.

FIG. 8 is a detailed perspective view of a locking mechanism on the "Y" connector of FIG. 7.

FIG. 9 is a transverse cross section taken along the line 9—9 in FIG. 7.

FIG. 10 is a detailed perspective view of another locking mechanism on the "Y" connector of FIG. 7.

FIG. 11 is an exploded transverse cross section corresponding to FIG. 9, illustrating removal of the "Y" connector from the catheter shaft.

FIG. 12 is a perspective view of the distal end of the catheter shaft after removal of the "Y" connector, illustrating a sealing member.

FIG. 13 is a longitudinal cross section of the removable "Y" connector, taken along the line 13—13 in FIG. 7.

FIG. 14 is a longitudinal cross section of the entire catheter, taken along the line 13—13 in FIG. 7.

FIG. 15 corresponds to FIG. 14, except that the guidewire is illustrated in place in the guidewire lumen.

FIG. 16 is a foreshortened side elevation of another embodiment of the catheter of the present invention.

FIG. 17 is a longitudinal cross-section of the catheter of FIG. 16, taken along the line 17—17.

FIG. 18 corresponds to FIG. 17, except a removable breakaway portion is shown in phantom.

FIG. 19 corresponds to FIG. 18, and illustrates lateral removal of a guidewire through a breakaway "Y" connector.

FIG. 20 corresponds to FIG. 19, further illustrating removal of the guidewire through the sidewall of the guidewire lumen.

FIG. 21 is an exploded view of the breakaway "Y" connector of the present invention.

FIG. 22 is a sectional view taken along the line 22—22 in FIG. 21.

FIG. 23 is a sectional view taken along the line 23—23 in FIG. 21.

FIG. 24 is a sectional view taken along the line 24—24 in FIG. 21.

FIG. 25 is a sectional view taken along the line 25—25 in FIG. 21.

FIG. 26 corresponds to FIG. 21, except that the breakaway portion of the "Y" connector is assembled with the remainder of the "Y" connector.

FIG. 29 is a partial transverse cross-section of one embodiment of the catheter shaft illustrating a removable longitudinal strip.

FIG. 30 corresponds to FIG. 29, illustrating a different kind of removable strip.

FIG. 31 corresponds to FIG. 29, further illustrating yet another type of removable strip.

DETAILED DESCRIPTION OF THE INVENTION

Figure 27:
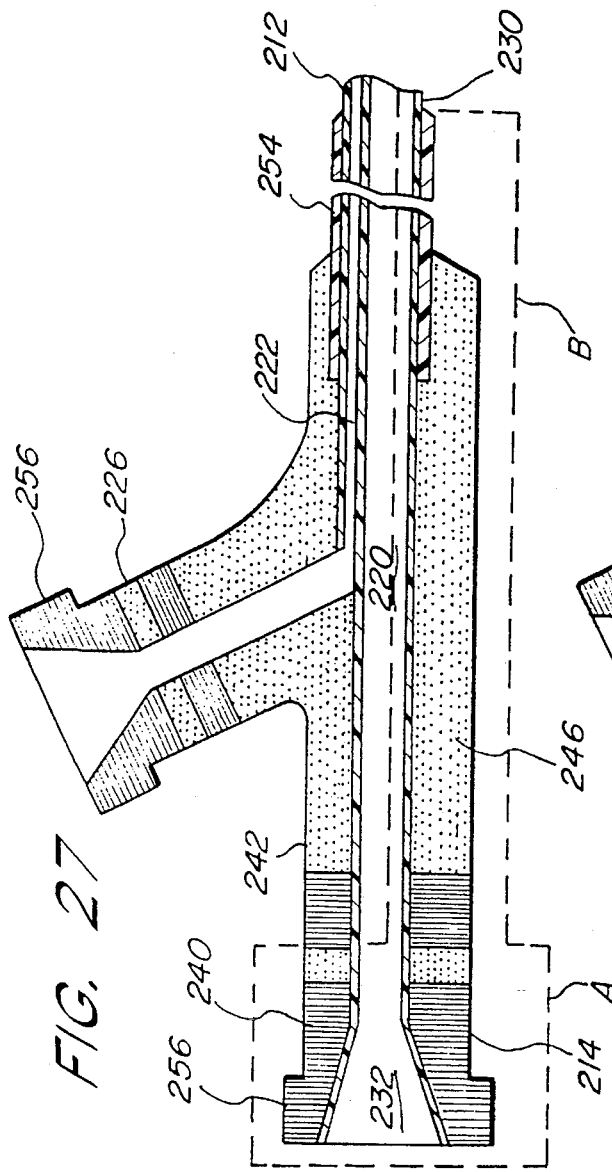
FIG. 27 is a cross-section taken along the line 27—27 in FIG. 26.

A basic embodiment of the catheter of the present invention is illustrated in FIG. 1. A catheter 10 is provided with a catheter shaft 12 extending from a proximal end 14 to a distal end 16. As shown more clearly in FIG. 1B, the interior of the catheter shaft 12 has a guidewire lumen 20 and a balloon inflation lumen 22 extending through the catheter shaft 12.

The catheter 10 has an angioplasty balloon 24 at the distal end 16 thereof. At the proximal end 14 of the catheter shaft 12, a balloon inflation connector 26 is provided in fluid communication with the balloon lumen 22. Fluid introduced into the proximal end of the balloon inflation connector 26 can travel through the balloon lumen 22 and into the interior of the balloon 24 to inflate and deflate the balloon 24 during an angioplasty procedure. The balloon inflation lumen 22 terminates inside the balloon 24. The opposite end of the balloon inflation lumen 22 terminates inside the balloon inflation connector 26.

The guidewire lumen 20 is adapted to receive a steerable guidewire and has an outside wall 30 (shown in FIG. 1B).

A proximal opening 32 is provided through the outside wall 30 of the guidewire lumen 20. This proximal opening 32 is situated in the proximal portion of the catheter shaft 12 at a location sufficiently close to the proximal end 14 that it is normally outside of the patient during the angioplasty (or other vascular procedure). Typically, the proximal opening 32 will be within 60 cm, preferably within about 40 cm, more preferable within about 30 cm of the proximal end 14 of the catheter 10.

The balloon 24 is made in accordance with conventional techniques for fabricating angioplasty balloons. Preferably, it is either blown from the distal end 16 of the catheter shaft 12, or is blown or formed of a separate piece of material which is bonded to the distal end of 16 of the catheter shaft 12. The balloon 24 may advantageously be formed of relative inelastic polymer material, such as polyethylene, polypropylene, polyvinylchloride, polyethylene terephthalate, and the like.

The catheter shaft 12 is also provided with a side port 34 which extends through the outside wall 30 of the guidewire lumen 20. The side port 34 is located distally of the proximal opening 32, and is located at a point normally inside of the patient when the catheter is properly in place for performance of angioplasty procedure. Preferably, the side port 34 is located proximally of the balloon 24 and within 80 cm, preferably 60 cm, and more preferably about 40 cm of the balloon 24. Alternatively, it is at least 5, 10, 15, 20, 25, 30, or at least 40 cm proximal of the balloon, or (increasing those numbers by about 5 cm) proximal of the distal end of the catheter.

The catheter 10 of the present invention is in some embodiments provided with a means for removing a guidewire that is inside of the guidewire lumen out of the guidewire lumen 20 through the outside wall 30 of the guidewire lumen 20. If the catheter shaft 12 or the guidewire is considered to extend in a longitudinal or axial direction, this movement of the guidewire out of the guidewire lumen 20 can be considered as a sideways, radial, or transverse motion of the guidewire. This means is referred to herein as "guidewire removing means." The guidewire removing means 40 is adapted to form a slit through the outside wall 30 of the guidewire lumen 20 through which the guidewire may be removed from inside the guidewire lumen 20. The guidewire removing means 40 may be an actual slit cut entirely through the side wall 30 of the guidewire lumen 20. Alternatively, it may be an inchoate slit such as the weakened area illustrated in FIG. 1B. The guidewire removing means 40 may be cut entirely through the outside wall 30 of the guidewire lumen 20 only in certain sections, leaving other section at least partially intact, to form a sort of perforated line. It may be formed of a different material than the remainder of the catheter shaft 12 and even of a different material than the adjacent portions of the outside wall 30 of the guidewire lumen 20. Combinations of fully formed slits and weakened areas or inchoate slits are also contemplated, such as having an inchoate slit in portions of the catheter normally outside the patient during use (eliminating backbleeding through the slit) and a fully formed slit in a portion of the catheter normally inside the patient during use.

One advantage of having only an inchoate slit is that it prevents backbleeding out of the guidewire removing means 40 during performance of the procedure. It is possible, however, to use an inchoate slit for only the portion of the guidewire removing means 40 that is outside of the guiding catheter in use. The remainder of the guidewire removing means 40 that is outside the patient and outside the guiding catheter can be a fully formed slit or a perforated slit without creating backbleeding problems. The guidewire removing means preferably extends the majority of the length of the catheter from a point at or adjacent to the proximal end of the catheter to a point proximal of the balloon.

As illustrated in FIG. 2, the guidewire removing means 40 may comprise a removable tear strip 42 defined by a pair of weakened lines 44, 46 extending distally from the proximal opening 32.

The guidewire removing means 40 extends from the proximal opening 32 distally along the length of the catheter shaft 12 to a point that is ordinarily inside the patient when the catheter 10 is properly placed for performance of an angioplasty procedure. Thus, the guidewire removing means 40 begins at a point ordinarily outside the patient and outside the guiding catheter upon proper placement of the catheter 10 and extends distally to a point ordinarily inside the patient upon such placement. From another perspective, it can be said that the guidewire removing means 40 extends distally for at least 40 cm, preferably at least 60 or 70 cm, and more preferably at least 80, 90 or 100 cm.

The guidewire removing means 40 may advantageously extend distally to the side port 34, and in one embodiment of the invention, may extend an additional distance distally beyond the side port 34. The guidewire removing means 40 preferably terminates proximally of the balloon 24, and may be immediately adjacent the balloon 24 or may be 5 cm, 10 cm, or more proximally of the balloon 24.

If the guidewire removing means 40 is not a slit prior to its use, it becomes a slit or opening after use, an illustrated in FIG. 1C.

The use of the catheter 10 of the present invention is illustrated in FIG. 3. In this longitudinal cross sectional view, the catheter 10 is illustrated with a guidewire 50 in place in the guidewire lumen 20. The proximal portion of the guidewire 50 is outside of the catheter 10. The guidewire 50 passes through the proximal opening 32 into the guidewire lumen 20, and is inside the guidewire lumen 20 for the entire length of the catheter shaft 12 that extends distally from the proximal opening 32. The distal end of the guidewire 50 extends out of the distal end 16 of the catheter shaft 12.

When the guide wire is to be removed radially or laterally out of the guidewire lumen 20, the guidewire removing means 40 provides a slit or opening in the outside wall 30 of the guidewire lumen 20 through which the guidewire 50 may be removed from the guidewire lumen 20. This slit or opening, if not fully formed, may be completed by cutting the outside wall 30 of the guidewire lumen 20, by tearing or rupturing a weakened area in the outside wall 30, or by tearing loose a removable strip (as illustrated in FIG. 2). In a preferred embodiment the guidewire removing means 40 is a weakened area that is fully opened only when the guidewire 50 is removed through the guidewire removing means 40. In one embodiment, the guidewire 50 is simply pulled through the outside wall 30 of the guidewire lumen 20. Alternatively, as illustrated in FIG. 4, the catheter shaft 12 may be provided with a filament 52 in association with the guidewire removing means 40. The filament 52 may be a continuous fiber or strand extending along the length of the guidewire removing means and inside at least a portion of the outside wall 30 of the guide wire lumen 20. When the filament 52 is pulled outwardly, it tears a slit into the outside wall 30 of the guidewire lumen 20.

In FIG. 3, the initial removal of the guidewire 50 through the guidewire removing means 40 is illustrated in phantom. In that figure, a phantom guidewire 50 is illustrated extending through the outside wall 30 of the guidewire lumen 20 at a point distally of the proximal opening 32.

As illustrated in FIG. 5, the phantom guidewire 50 is pulled through the outside wall 30 of the guidewire lumen 20 until the guidewire 50 has been removed through the outside wall 30 up to the side port 34. It will be understood, of course, that in accordance with the present invention, the guidewire 50 may be removed through the outside wall 30 to a point proximal of or distal of the side port 34. In a first discussed preferred embodiment, the lateral removal out of the guidewire lumen 20 continues up to the side port 34. In a second discussed preferred embodiment, the lateral removal of the guidewire continues to a point proximal of the side port.

It should be noted that the removal of the guidewire 50 through the outside wall 30 can be accomplished without longitudinal or axial movement of the guidewire 50. Thus, in FIG. 3, the distal tip of the guidewire 50 is in the same position as in FIG. 5; however, in FIG. 5, the guidewire has been removed laterally through the guidewire removing means along a portion of the length of the catheter shaft 12.

In the simplest embodiment of the present invention the guidewire lumen 20 may be provided simply with a proximal opening 32, a side port 34, and guidewire removing means 40 extending distally of the proximal opening 32 at least to the side port 34, and perhaps beyond.

However, more sophisticated versions of the present invention are also contemplated. In one such embodiment, a distal side opening 54 may be provide through the outside wall 30 of the guidewire lumen 20 to provide access into the guidewire lumen 20 at a point distal of the sideport 34. The distal side opening 54 may be open in normal use; however, the distal side opening 54 is preferably covered with a removable patch 56, as best seen in FIGS. 3 and 5. The removable patch 56 is preferably made of foil, mylar, aluminized or metalized mylar, or other suitable material, and may be held in place with an adhesive. The removable patch 56 may be removed from the catheter shaft 12 to open up the distal side opening to permit extension of the guidewire 50 through the distal side opening or to permit use of the distal side opening 54 as a perfusion opening. In one embodiment of the invention, the guidewire removing means 40 extends distally to the distal side of opening 54.

The portion of the guidewire lumen 20 located proximally of the proximal opening 32 is preferably closed, and may be filled with a filler 60 such as a polymer material formed in place or a stylet inserted in a waterproof manner into a guidewire lumen 20, as illustrated in FIGS. 3 and 5.

In an alternative embodiment of the invention, the catheter of FIG. 1 is modified at its proximal end as illustrated in FIG. 6. Specifically, this particular catheter has a conventional "Y" connector 62 at the proximal end 14 of the catheter shaft 12 having a balloon inflation connector 26 and a guidewire connector 64 at the two "branches" of the "Y". The guidewire lumen 20 extends from the proximal end 14 of the catheter shaft 10 through the guidewire connector 64 and the "Y" connector 62 and extends distally the length of the catheter shaft 12.

The proximal opening 32 is located distally of the "Y" connecter. The catheter 10 is provided with a sliding cover 66 that is axially movable to cover or uncover the proximal opening 32. The sliding cover 66 is preferably an annular sleeve circling the catheter shaft 12 and axially movable with respect thereto. The sliding cover 66 preferably has a soft sealing material 70 (such as a pliable closed cell polymer foam, a silicone elastomer, or other suitable material) on its inside surface to provide a seal against the catheter shaft 12. Ordinarily, the sliding cover 66 is over the proximal opening 32, closing and sealing the proximal opening 32.

In an alternative embodiment, the sliding cover 66 may be replaced by a removable covering (not illustrated) similar to the removable patch 56 to close the proximal opening 32 until it is used.

In ordinary use, the guidewire 50 extends distally through the guidewire connector 64, the remainder of the "Y" connector 62, inside the guidewire lumen 20, past the proximal opening 32, and out of the distal end 16 of the catheter 10. When required (as will be explained in more detail hereafter), the sliding cover 66 or other seal covering the proximal opening 32 is removed, the catheter 10 is maintained in place in the patient while the guidewire 50 is removed proximally out of the guidewire connector 64, and the guidewire 50 is then inserted through the proximal opening 32 until it is in the desired position. Then the guidewire 50 is removed out through the outside wall 30 of the guidewire lumen 20 as explained in more detail elsewhere. Removal of the guidewire 50 through the outside wall of the catheter shaft 12 permits conversion of the catheter from an over-the-wire catheter to a rapid exchange catheter that can be removed from the patient without extension of the guidewire 50.

In the embodiment illustrated in FIG. 6, because a conventional guidewire connector 64 is ordinarily used, back bleeding during use is eliminated by tightening the Tuehy-Borst adapter (not shown) except when manipulating the guidewire 50. This is in contrast to the embodiment illustrated in FIG. 1, where some back bleeding might be expected.

In yet another embodiment of the invention, the guidewire removal and reinsertion explained in connection with FIG. 6 is eliminated by providing a removable "Y" connector 80, illustrated in FIGS. 7–13.

The particular embodiment of removable "Y" connector illustrated in FIG. 7 provides an axially separable "Y" connector 80. The "Y" connector 80 is preferably molded of a relatively hard thermoplastic material, and is adapted to fit concentrically around the catheter shaft. The removable "Y" connector 80 is formed of 2 (or more) pieces which are joined together along lines extending in the axial or longitudinal direction of the catheter shaft 12. In the illustrated embodiment, the removable "Y" connector has an axial portion 82 through which the balloon lumen 22 (and preferably the catheter shaft 12) extends. The removable "Y" connector 80 further has a guidewire connector 64 extending proximally and at an angle outwardly from the axial portion 82 of the removable "Y" connector 80.

The guidewire connector 64 of the removable "Y" connector 80 is cylindrical in shape and has a guidewire bore 84 extending therethrough. The guidewire bore 84 connects through the proximal opening 32 into the guidewire lumen 20, as best illustrated in FIG. 13.

The removable "Y" connector 80 is preferably formed of a first half 86 and second half 90. The first half 86 and the second half 90 each have a semi cylindrical recess 92, 94 extending axially along the length of each half 86, 90 of the removable "Y" connector 80. The semi cylindrical recesses 92,94 are best illustrated in FIG. 11. When the first and second halves 86, 90 are joined together, the semi cylindrical recesses 92, 94 together form a cylindrical recess through which the catheter shaft 12 extends.

When the first and second halves 86, 90 are joined together on the catheter shaft 12, they are joined at a first edge 96 and a second edge 100 on opposite sides of the catheter shaft 12. The first and second edges 96, 100 of each half 86, 90 extend axially parallel to the axis of the catheter shaft 12.

In a preferred embodiment of the invention, the first edges 96 of the first and second halves 86, 90 are joined by a hinge 102. Preferably, the hinge 102 is a "live" hinge; that is, a hinge formed of a thin portion of the polymer material of which the removable "Y" connector 80 is formed. In a preferred embodiment, the hinge 102 extends axially the entire length of the first edge 96.

The second edges 100 of the first and second halves 86, 90 are separably joined together by any appropriate connecting mechanism. The illustrated mechanism is but one possibility. In the illustrated mechanism, the second edge 100 of the first and second halves 86, 90, comprises on each half a radially extending tab 104 running the length of the second edge 100. At the outside radial edge of the tabs 104 is a flange 106 formed so that when the first and second halves 86, 90 are mated together at their second edges 100, the flanges 106 extend in opposite directions on the first and second halves 86, 90, forming a "T" shape in radial cross section as shown in FIG. 9.

An edge connector 110 is provided to hold the second edges 100 of the first and second halves 86, 90 together. The edge connector 110 preferably extends the entire length of the second edges 100 and is formed with a "T" channel inside to lock together the tabs 104 and flanges 106 of the second edges 100 of the first an second halves 86, 90. Thus, the "T" of the mated second edges of the second edges 100 of the first and second halves 86, 90 is adapted to slide inside the "T" channel of the edge connector 110. Once the connector 110 is placed on the "T" of the second edges, it may be locked in place using any appropriate mechanism. In one embodiment, a first end 112 of the connector is permanently closed to prevent movement of the edge connector 110 in one direction. The second end 114 of the edge connector 110 may have a breakaway end 116, as illustrated in FIGS. 7 and 8. The breakaway end 116 is glued or otherwise connected to the remainder of the connector 110 in such a manner that it may be readily severed from the edge connector 110. This may be done by a rocking motion applied to the breakaway end 116 as illustrated in by the arrows 120 in FIG. 7. Once the breakaway end 116 is removed as illustrated in FIG. 8, the connector 110 may be moved axially in the direction indicated by arrow 122 until the edge connector 110 is removed from the remainder of the removable "Y" connector 80.

Another method for locking the edge connector 110 onto the removable "Y" connector 80 is by use of a locking pin 124 as illustrated in FIG. 10. The locking pin may extend through the edge connector 110 and the second edges 100 of the first and second halves 86, 90, to lock the edge connector 110 in place. When the pin 124 is removed, the edge connector 110 may also be removed.

Although the pin 124 illustrated in FIG. 10 is circular, any other suitable pin or locking device may similarly be used.

After the removal of the edge connector 110, the first and second halves 86, 90 may be removed from the catheter shaft 12 as illustrated in FIG. 11 by pivoting the second edges 100 away from each other. The removable "Y" connector 80 may then be slid proximally off the proximal end of the guidewire 50.

In a preferred embodiment of the invention, a seal 126 is provided around the catheter shaft 12 as illustrated in FIG. 12. The seal 126 prevents leakage between the removable "Y" connector 80 and the catheter shaft 12, and is preferably formed of annular polymer material such as elastomeric material or closed cell foam. The seal 126 is preferably provided with an index feature 130 for preventing rotational or longitudinal movement of the in-place "Y" connector 80 with respect to the catheter shaft 12. In the illustrated embodiment, the index feature 130 is an outwardly extending tab; however, the index feature 130 could alternatively be a groove, a recess, a flange, or the like. The outwardly-extending index feature 130 illustrated in FIGS. 12 and 11 can cooperate with a complimentary index receptacle 132 on the axial portion 82 of the removable "Y" connector 80.

The use of the removable "Y" connector is further illustrated in FIGS. 14 and 15. The catheter 10 with the "Y" connector 80 in place is illustrated in FIGS. 14 and 15. A guidewire 50 is inserted into the proximal opening 32 through the guidewire adapter 64, as seen in FIG. 15. The guidewire 50 extends the length of the catheter shaft 12 and out of the distal end 16 of the catheter 10.

When the removable "Y" connector 80 is removed from the catheter shaft 12, the catheter 10 is properly illustrated in FIG. 3, and the guidewire 50 can be removed laterally through the outside wall 30 of the guidewire lumen 20 as illustrated in FIGS. 3 and 5, and as previously explained.

Although the removable "Y" connector 80 has been discussed in the context of a particular preferred embodiment, it will be understood that equivalent removable "Y" connectors can be provided in which only a portion (such as a strip) of the "Y" connector is removed from the catheter shaft 12; or where there are more than 2 separably pieces of the "Y" connector; or where alternative latches or locking mechanisms are utilized to hold the removable "Y" connector together until removal is desired. Further, other mechanical features having equivalent function can be substituted for other of the various described elements.

A catheter according to the invention having another version of the "Y" connector is illustrated in FIGS. 16 and 17. This embodiment of the invention is referred to as the "universal mode" vascular catheter.

In this embodiment of the invention, a catheter 210 is provided with a catheter shaft 212 having a proximal end 214 and a distal end 216. The catheter shaft 212 is provided with a guidewire lumen 220 and a balloon lumen 222 extending the length of the catheter shaft 212. A conventional angioplasty balloon 224 is provided at the distal end 216 of the catheter shaft 212. The balloon 224 is inflated by introducing pressurized fluid through the balloon inflation connector 226 located at the proximal end 214 of the catheter shaft 212. Such pressurized fluid travels distally from the balloon inflation connector 226 through the balloon inflation lumen 222 which communicates with the interior of the balloon 224.

The guidewire lumen 220 has an outside wall 230, and a proximal opening 232.

The catheter 210 is also provided with a side port 234 providing an opening through the outside wall 230 of the guidewire lumen 220.

The side port 234 corresponds to the side port 34 previously described, and is adapted to permit insertion or removal of a guidewire therethrough. Preferably, the side port 234 is configured such that a guidewire passing through the side port 234 may easily extend distally through the guidewire lumen 220, but is adapted to discourage a guidewire passing through the side port 234 from extending proximally through the guidewire lumen 220 from the side port 234. The location of the side port 234 is as previously described in connection with the side port 34.

The guidewire lumen 220 extends substantially the entire length of the catheter shaft 212 from the proximal opening 232 through the balloon 234 to a distal opening 236 located distally of the balloon 224.

Located at the proximal end 214 of the catheter 210 is a guidewire connector 240 adapted to provide access to the guidewire lumen 220. The proximal opening 232 of the guidewire lumen 220 is a channel extending through the guidewire connector 240. The guidewire connector 240 may advantageously be located proximally of the balloon inflation connector 226; however, it is also contemplated that the guidewire connector 240 may be located distally of the balloon inflation connector 226.

In one preferred embodiment of the invention, the guidewire connector 240 and the balloon inflation connector 226 together comprise a "Y" connector 242 as illustrated in FIG. 17. In the preferred embodiment of the "Y" connector 242, the guidewire connector 240 and the balloon inflation connector 226 are connected together and are formed of an appropriate material such as a molded polymer material. The guidewire connector 240, for example, may be coaxial with the guidewire lumen 220, while the balloon inflation connector 226 may extend at an angle from the balloon inflation lumen 222. In this manner, the connectors 226, 240 together form a "Y".

As illustrated in FIG. 18, one preferred embodiment of the universal mode catheter 210 includes a "Y" connector 242 having a breakaway piece 246. The breakaway piece 246 is illustrated in FIG. 18 in phantom. As illustrated, when the breakaway piece of the "Y" connector 242 is removed, the outside wall 230 of the guidewire lumen 220 is exposed for its entire length. The breakaway piece 246 can be completely removed from the remainder of the "Y" connector, or it may be hinged to simply pivot away from the remaining portion of the connector.

The outside wall 230 of the guidewire lumen 220 in this embodiment of the invention is provided with guidewire removing means 250. The guidewire removing means 250 corresponds to the guidewire removing means 40 previously discussed. As illustrated in FIG. 19, when a guidewire 252 is in place in the guidewire lumen 220, the breakaway piece 246 can be removed from the guidewire connector 240 so that the guidewire 252 can be moved laterally through the guidewire removing means 250 through the outside wall 230 of the guidewire lumen 220. (The guidewire extending through the guidewire lumen 220 from the proximal end 214 is illustrated in phantom; the solid guidewire 252 is illustrated after lateral removal from the portion of the guidewire lumen 220 out of the guidewire connector 240 and the "Y" connector 242.)

FIG. 20 illustrates further removal of the guidewire 252 laterally through the outside wall 230 of the guidewire lumen 220 by means of the guidewire removing means 250. In FIG. 20, the guidewire 252 is illustrated in a phantom starting position corresponding to the guidewire in FIG. 19, and in solid illustrating further removal laterally through the guidewire removing means 250 until the guidewire 252 is extending through the side port 234. Removal of the guidewire 252 through the guidewire removing means 250 is accomplished in the same manner as previously discussed.

The breakaway connector 242 of this embodiment of the invention is illustrated in more detail in FIGS. 20-25.

FIG. 21 is a perspective view of the "Y" connector 242 from the side opposite the balloon inflation connector 226 (which is hidden in FIG. 21). In FIG. 21, the guidewire connector 240 is provided with a removable breakaway piece 246 on the side of the guidewire connector 240 opposite the balloon connector 226. The guidewire connector 240 is preferably formed of injection-molded thermal plastic material. In a preferred embodiment, it is formed integrally with the remainder of the "Y" connector 242. At the distal end of the "Y" connector 242 (where it meets the catheter shaft 212) a stress relief sleeve 254 may advantageously be provided. The stress relief sleeve 254 may be formed of flexible polymer material. It advantageously encircles the catheter shaft 212 from a point inside the dial end of the "Y" connector 242 extending a short distance (e.g. 1–2 cm) distally of the "Y" connector 242 to prevent buckling of the catheter shaft 212.

The removable breakaway piece 246 preferably overlays a portion of the outside wall 230 of the guidewire lumen 220. In radial cross-section the breakaway piece 246 may, for example, comprise from about 5° to about 180° of arc. In the embodiment illustrated in FIG. 21, the breakaway piece 246 encircles the catheter shaft 212 for about 90° to 120° of arc. Although the longitudinally extending breakaway piece 246 is shown extending the entire length of the "Y" connector 242, it should be understood that a "Y" connector having an axially removable proximal portion (outlined by dashed line "A" in FIG. 27) that entirely encircles a guidewire and a longitudinally extending, radially removable portion (outlined by dashed line "B" in FIG. 27) is also contemplated. To use this embodiment, the encircling proximal portion "A" is removed axially, and the longitudinally extending portion "B" is removed radially. In another variation of this embodiment, the portion "B" may simply be eliminated, leaving a slot, and the lateral or radial removal of the guidewire 252 from the "Y" connector can be accomplished after removing portion "A" (as by unscrewing it from the remainder of the "Y" connector 242 and sliding it off of the proximal end of the guidewire 252).

The breakaway piece 246 may advantageously be formed from the same material as the remainder of the "Y" connector 242. It may be molded separately from the remainder of the "Y" connector 242; alternatively, the "Y" connector may be molded in one piece, and then the breakaway piece 246 may be cut from the "Y" connector 242. The catheter may even be provided with the breakaway piece 246 entirely missing. In this embodiment, a narrow longitudinal slot is provided along the side of the "Y" connector at all times. The proximal end of the guidewire connector 240 may then be removable and may completely encircle the guidewire.

In any event, means (not illustrated) for holding the breakaway piece 246 in place until removal is desired should be provided. These means may include a relatively weak adhesive or weld joining the edges of the breakaway piece 246 to the corresponding edges of the remainder of the "Y" connector 242. Alternately, the breakaway piece 246 may be incompletely cut from the remainder of the "Y" connector 242. In another embodiment, the breakaway piece 246 may be held in place by tape encircling the breakaway piece 246 and all or part of the guidewire connector 240 and/or the "Y" connector 242.

The guidewire connector 240 preferably has a circular flange encircling the proximal end thereof to facilitate connection of adapters and the like.

When the breakaway piece 246 is removed from the guidewire connector 240 and/or the "Y" connector 242, the guidewire removing means 250 will be exposed. As previously discussed, the guidewire removing means may be a slit, a weakened line, a tear-away strip, or other equivalent means for removing the guidewire 252 laterally through the outside wall 230 of the guidewire lumen 220.

In addition to removing the breakaway piece 246, at least a portion of the stress relief sleeve 254 must also be removed, as also illustrated in FIG. 21. The stress relief sleeve 254 may be slit or cut and the removable portion may be connected to the breakaway piece 246. Alternatively, the stress relief sleeve 254 may simply be slit and not removed from the outside wall 230 of the guidewire lumen 220.

The construction of the breakaway "Y" connector is further illustrated in cross-section in FIGS. 22–24.

In FIG. 22, the proximal end of the guidewire connector 240 is illustrated, showing the unitary polymer construction thereof. In FIG. 23, the unitary guidewire connector 240 is shown encircling only the guidewire lumen 220 of the catheter shaft 212.

In FIG. 24, the balloon inflation connector 226 is shown extending from the far side of the "Y" connector 242. The guidewire connector portion of the "Y" connector 242 is shown encircling both the guidewire lumen 220 and the balloon inflation lumen 222. The stress relief sleeve 254 is shown between the guidewire connector 240 and the catheter shaft 212.

Finally, in FIG. 25, the catheter shaft distal of the "Y" connector 242 is illustrated, showing the guidewire lumen 220, the balloon inflation lumen 222, and the outside wall 230 of the catheter shaft 212.

FIG. 26 is an illustration of the "Y" connector 242 assembled together with the breakaway piece 246. The stress relied sleeve 254 is illustrated partially cut away. This partial cut-away of the portion of the stress relief sleeve 254 may represent the actual finished product. In other words, the finished product may have the portion of the stress relief sleeve 254 overlying the guidewire removing means 250 removed. Alternatively, that portion of the stress relief sleeve 254 may be removable when the breakaway piece 246 is removed.

FIG. 27 is a longitudinal cross-section of the "Y" connector 242. It illustrates the placement of the stress relief sleeve 254 partially inside the "Y" connector 242. Connector flanges 256 are provided on both the guidewire connector 240 and the balloon inflation connector 226. In order to facilitate insertion of the guidewire 252 and connection to appropriate connectors and adapters, the proximal opening 232 of the guidewire lumen is preferably flared so that the channel extending through the guidewire connector is wider at its proximal end 214.

Figure 28:
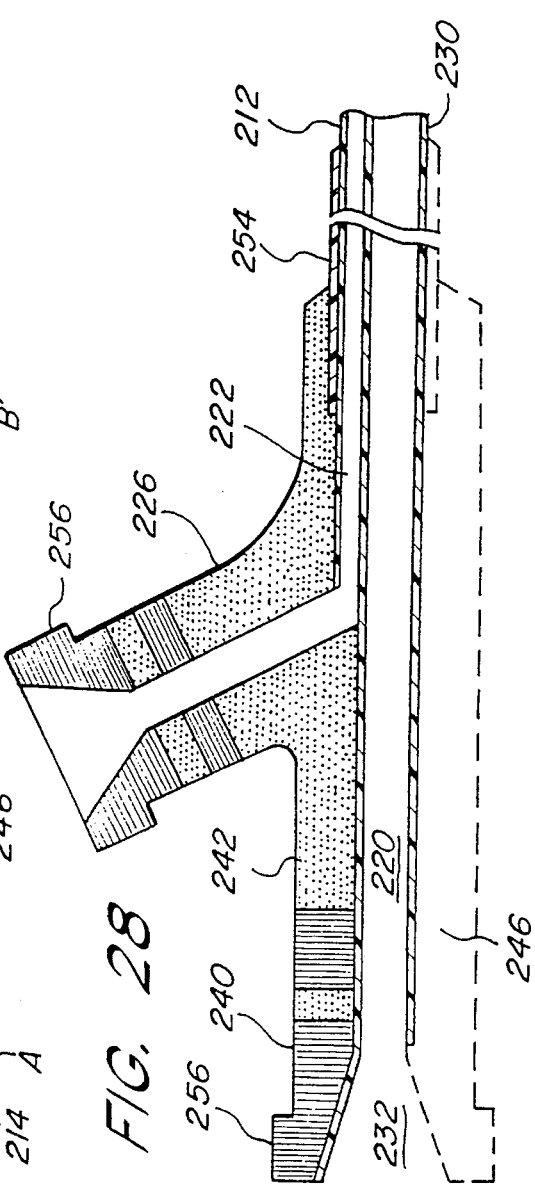
FIG. 28 corresponds to FIG. 27, except that the breakaway portion of the "Y" connector has been removed and is illustrated in phantom.

FIG. 28 corresponds to FIG. 27, except that the breakaway piece 246 has been removed and is illustrated in phantom.

FIG. 29 illustrates yet another embodiment of the guidewire removing means 250. In this illustrated embodiment, the outside wall 230 of the guidewire lumen 220 is provided with two weakened areas 260, 262 extending parallel and longitudinally along the outside wall 230 of the guidewire lumen 220. In a preferred embodiment, the weakened areas 260, 262 each comprise a juxtaposed pair of continuous or interrupted grooves formed in the outside wall 230, one inside the wall and the other outside the wall 230. An optional reinforcing filament 264 is provided in the segment of the outside wall 230 located between the weakened areas 260, 262. The reinforcing filament 264 may advantageously comprise a high tensile strength thread or filament, such as nylon or polyaramid (e.g., the material sold by du Pont under the trademark KEVLAR). Alternatively, it may be formed of metal.

The portion of the outside wall 230 bounded by the weakened areas 260, 262 comprises a tear-away strip 266. This strip 266 may be the same thickness as the remainder of the catheter shaft wall; it may be thinner; or it may be thicker. In use, the tear-away strip may be removed by grasping it at the proximal end and tearing distally. Alternatively, it may be removed simply by pulling the guidewire laterally through the outside wall 230 of the guidewire lumen, pulling the tear-away strip 266 in the process.

Another version of the tear-away strip 266 is illustrated in FIG. 30. In this embodiment, the tear-away strip 266 is formed of a different material than the remainder of the outside wall 230 of the guidewire lumen 220. This particular tear-away strip 266 may be formed, for example, by co-extruding a second material with the catheter shaft 212. The portions of the outside wall 230 adjacent to the guidewire removing means 250 are separated by the width of the tear-away strip 266, and the tear-away strip 266 overlaps the outside wall 230 on both the inside and outside of the outside wall 230. This overlapping, interlocking feature anchors the tear-away strip 266 to the outside wall 230 until removal is desired.

Still another embodiment of the tear-away strip 266 is illustrated in FIG. 31. In this embodiment, the tear-away strip 266 (which is advantageously formed of a separate or different material from the outside wall 230) is adhesively attached to the outside wall 230. It may be removed in a manner similar to that discussed in connection with FIGS. 29 and 30.

Whether the catheters of the present invention include a tear-away strip or a slit (formed or inchoate) as the guidewire removing means, it should be understood that the side port is optional when the catheter is used as an over the wire catheter. The side port is useful, however, when one inserts the catheter in rapid exchange mode, with the guidewire passing through the outside wall of the guidewire lumen into the guidewire lumen at a point on the catheter that is ordinarily inside the patient during use of the catheter.

There are many alternative geometries that can be used for the side ports 34, 234, which are applicable to all of the catheters described herein. For example, sideport 34, 234 may not comprise an actual opening, but rather a slit. One configuration of a slit that is adapted for easy insertion and removal of a guidewire is a "Y" shape, where the stem of the "Y" is a guidewire removing means slit or strip 40, 250 and the two arms of the "Y" extend at divergent angles from the stem. The slits may be fully formed; alternatively, they can be interrupted slits or weakened areas. It will be appreciated that there is no opening or hole in the outside wall of the guidewire lumen; rather, the edges of the slits are closed until a guidewire is passed through this version of the "side port" 34, 234.

Another embodiment of the side port 34, 234 is contemplated wherein the sideport 34, 234 is initially closed, and is part of the outside wall 30, 234 of the guidewire lumen 20, 220. Until then, the sideport 34, 234 is inchoate. When one desires to use the sideport 34, 234, the material closing the sideport 34, 234 is removed to open that side port. Thus, the sideport 34, 234 may be defined by a perforated line (interrupted slit), a weakened area, or the like. It can be connected to a single slit guidewire removing means 50, 250 or to any of the other guidewire removing means disclosed herein. Where the guidewire removing means is a tear-away strip, the sideport 34, 234 can be connected to and be a part of that strip, and may either be the same size as or an enlarged portion of that strip.

Figure 32:
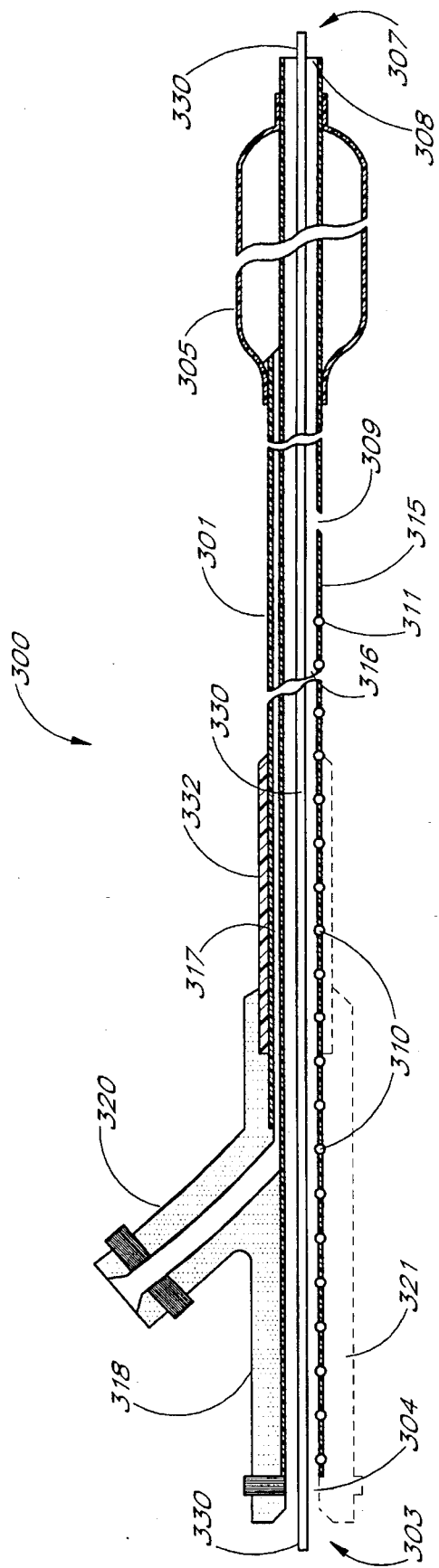
FIG. 32 is a cross-sectional view of an alternative preferred embodiment of the catheter of the present invention with a guidewire extending through the guidewire lumen.
Figure 33:
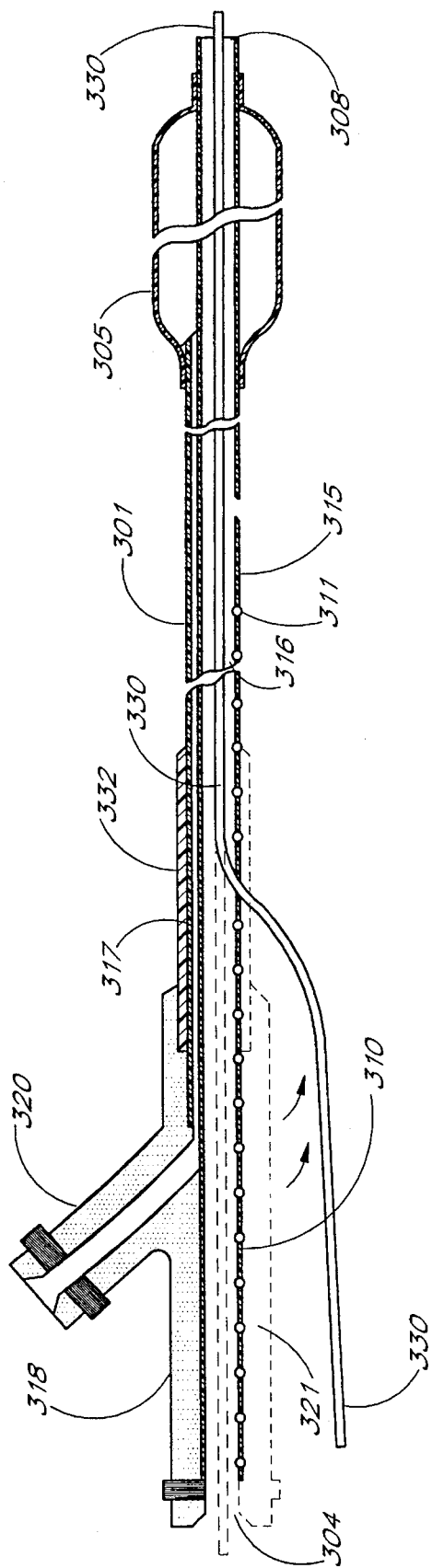
FIG. 33 is a cross sectional view of the catheter in FIG. 32 showing removal of the guidewire through the guidewire removing means.
Figure 34:
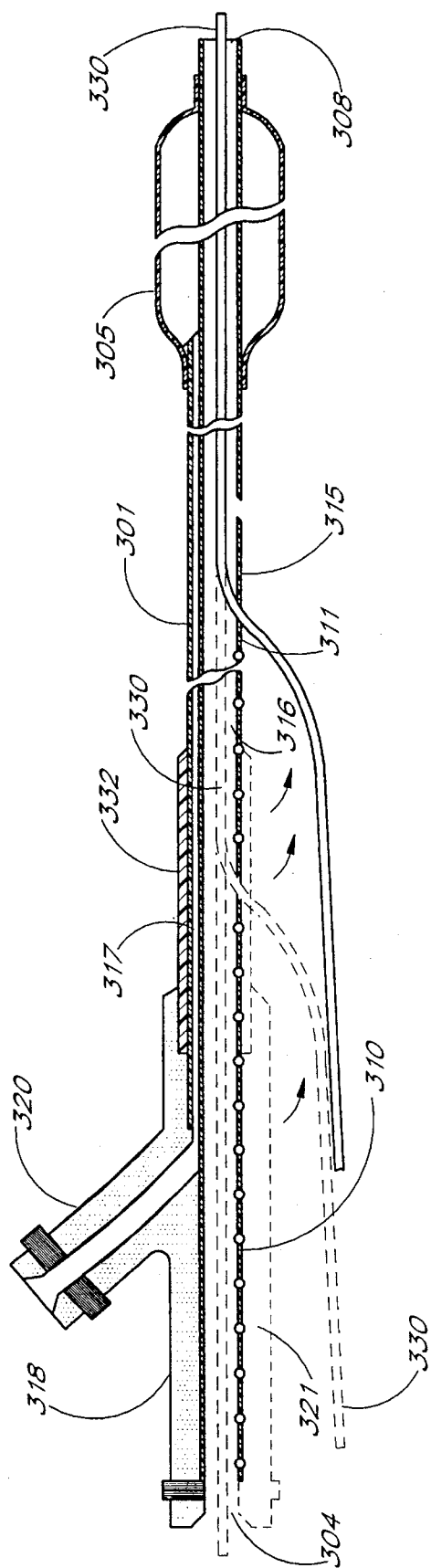
FIG. 34 is a cross sectional view of the catheter in FIG. 33 showing additional removal of the guidewire through the guidewire removing means.

In FIGS. 32–34 another preferred embodiment of a catheter in accordance with the present invention is depicted.

According to this embodiment, the catheter 300 is provided with a catheter shaft 301 extending from a proximal end 303 on a proximal portion to a distal end 307 on a distal portion. The catheter shaft 301 has an outer wall 315. Within the catheter shaft 301 and the outer wall 315, extends a guidewire lumen 316 and a balloon inflation lumen 317. In a preferred embodiment, the guidewire lumen 316 preferably extends from a proximal opening 304 in the proximal portion of the catheter shaft 301 and through the catheter shaft 301 to a distal opening 308 in the distal end 307 of the catheter shaft 301. The guidewire lumen 316 is adapted to receive a steerable guidewire.

The proximal opening 304 is provided through the outside wall 315 of the guidewire lumen 316 or is provided at the proximal end 303 of the catheter shaft 301. This proximal opening 304 is situated in the proximal portion of the catheter shaft 301 at a location sufficiently close to the proximal end 303 that it is normally outside of the patient during the angioplasty procedure (or other vascular procedure). Typically, the proximal opening 304 will be within 60 cm, preferably within about 40 cm, more preferably within about 30 cm of the proximal end 303 of the catheter 300. In the preferred embodiment, the proximal opening 304 is located in the proximal end 303 of the catheter shaft 301.

Figure 39:
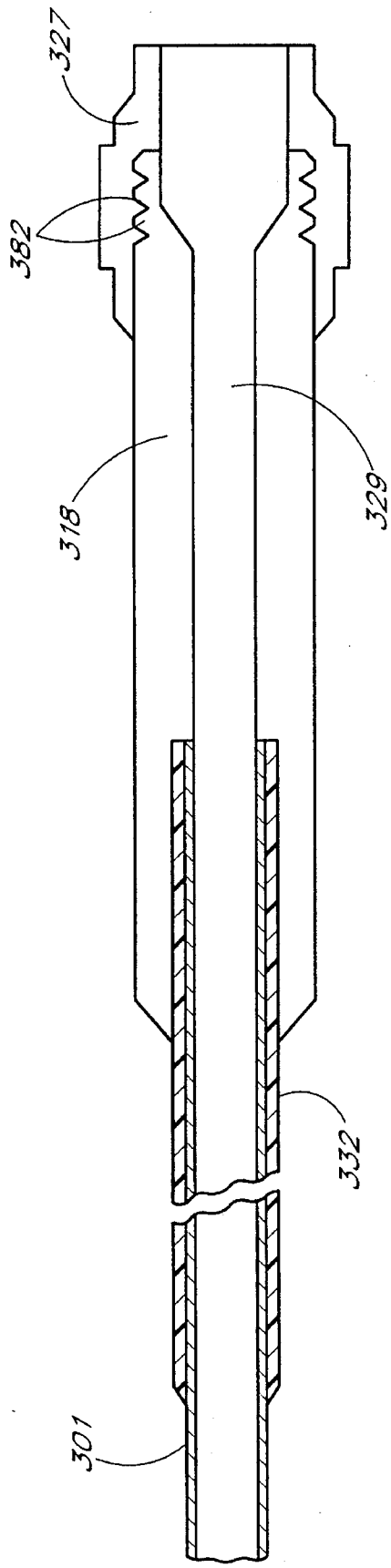
FIG. 39 is a longitudinal cross sectional view of the connector housing in FIG. 38 taken along line 44—44.

A connector housing 318 is preferably used in conjunction with the catheter. The connector housing 318 has a channel 329 (see also FIGS. 35 and 39) that is adapted to direct a guidewire into the guidewire lumen 316. The connector housing 318 is also used in association with a strain reliever 332 that helps to alleviate stress that would occur at the connection between the relatively flexible catheter shaft 301 and the relatively less flexible connector housing 318. In a preferred embodiment, the connector housing 318 and the strain reliever 332 each are equipped with guidewire removing means, which in a highly preferred embodiment comprises a removable wall section 321 that is shown removed in FIG. 34.

In a preferred embodiment, an angioplasty balloon 305 is mounted on the proximal portion near the distal end 307. Typically, on the proximal portion of the catheter shaft 301, a balloon inflation connector 320 in a connector housing 318 is provided in fluid communication with the balloon inflation lumen 317. Fluid introduced into the proximal end of the balloon inflation connector can travel through the balloon lumen 317 and into the interior of the balloon 305 to inflate and deflate the balloon 305 during an angioplasty procedure. The balloon inflation lumen 317 terminates inside the balloon 305. The opposite end of the balloon inflation lumen 317 terminates inside the balloon inflation connector in the connector housing 318.

The portion of the balloon inflation lumen 317 located proximally of its proximal opening in the connector housing 318 is preferably closed, and may be filled with a filler such as a polymer material formed in place or a stylet inserted in a waterproof manner into the balloon inflation lumen, as was previously discussed in connection with the guidewire lumen, as illustrated in FIGS. 3 and 5. Alternatively, the connector can be mounted on the proximal end of the catheter and the connector can be manufactured with two channels; a first channel that is constructed to direct a guidewire into the guidewire lumen in the proximal end of the catheter and a balloon inflation channel in sealing communication with the balloon inflation lumen in the proximal end of the catheter.

The balloon 305 is made in accordance with conventional techniques for fabricating angioplasty balloons, as discussed above. As will be appreciated, there are a variety of conventional balloon sizes. For example, coronary angioplasty balloons are typically between about 1 cm to 3 cm in length. However, in some applications, balloons greater than 3 cm are used, such as balloons between about 3 cm to 4 cm or even balloons between about 4 cm to 6 cm in length. Therefore, in general, it can be said that typical balloons will measure between about 1 cm and 6 cm in length.

On the distal end of the catheter shaft, distal to the balloon, there is a relatively short section of catheter shaft, referred to herein as a distal tip section. The distal tip section is useful for both providing a binding position for the distal side of the balloon, as well as assisting in torque functions with the guidewire against the catheter tip without damaging the balloon.

Typically, the distal tip section is less than 2 cm in length, more preferably it is less than 1 cm in length, and even more preferably, the distal tip section is 0.5 cm or less in length. It will be appreciated that the length limitations on the distal tip section are largely related to the size and contour of vessels in which the procedure is being undertaken. For example, in peripheral angioplasty, a longer distal tip section will ordinarily not impact the procedure. However, in coronary angioplasty, because of the small vessel size and the often tortious contours, short distal tip section lengths are preferred.

Accordingly, the proximal side of the balloon can be said to be positioned at a point distance between about 1.5 cm to about 8 cm from the distal end of the catheter shaft. In highly preferred embodiments, this point is between about 2.5 cm and 5 cm.

Referring again to FIG. 32 the catheter shaft 301 is also provided with a side port 309 which extends through the outside wall 315 of the guidewire lumen 316. The side port 309 is located distally of the proximal opening 304, and is located at a point normally inside the patient when the catheter is properly placed for performance of an angioplasty procedure. Preferably, the side port 309 is located proximally of the balloon 305 and at a (distance B) within 80 cm, preferably within 60 cm, and more preferably within about 40 cm of the proximal end of the balloon 305. In a highly preferred embodiment, the side port 309 is located within 10 cm. of the distal end 307 of the catheter shaft 301, and even more preferably within 8 cm. of the distal end 307 of the catheter shaft 301. In a highly preferred embodiment, the side port 309 is located within 7 cm. of the distal end 307 of the catheter shaft 301, i.e., at a distance which is the sum of distance a and distance b. Viewed in another manner, the side port is preferably positioned between about 2 cm and 5 cm proximal of the proximal side of the balloon, i.e., distance b.

The catheter 300 of the present invention is preferably provided with a guidewire removing means, as discussed above, for removing a guidewire that is extending through the guidewire lumen 316 through the outside wall 315 of the guidewire lumen 316, so that the guidewire no longer extends therethrough.

The guidewire removing means 310 extends from the proximal opening 304 distally along the length of the catheter shaft 301 to a point that is ordinarily inside the patient when the catheter 300 is properly placed for performance of an angioplasty procedure. Thus, the guidewire removing means 310 begins at a point ordinarily outside of the patient and outside the guiding catheter upon proper placement of the catheter 300 and extends distally to a point ordinarily inside the patient upon such placement. From another perspective, it can be said that the guidewire removing means 310 extends distally for at least 40 cm, preferably at least 60 or 70 cm, and more preferably at least 80, 90 or 100 cm. From still another perspective, the guidewire removing means in a preferred embodiment preferably extends along the majority of the catheter shaft to a point proximal of the balloon and proximal of the side port (if any).

In a preferred embodiment, the guidewire removing means extends distally from the proximal end 303, i.e., beginning at the proximal opening 304, of the catheter shaft 301. This arrangement enables a user to simply remove or push the guidewire out of the catheter shaft from the proximal end 303 to the termination point 311 of the guidewire removing means 310, avoiding many of the complications attendant in the prior art.

The guidewire removing means 310 may advantageously extend distally to the side port 309, and in one embodiment of the invention, may extend an additional distance distally beyond the side port 309. The guidewire removing means 310 preferably terminates proximally of the balloon 305, and may be immediately adjacent the balloon 305 or may be 5 cm, 10 cm, or more proximally of the balloon 305.

In a preferred embodiment, the guidewire removing means 310 terminates proximally of the side port 309. The distance between the side port and the termination point 311 of the guidewire removing means 310 is advantageously between 0.1 cm. and 40 cm. However, the guidewire removing means 310 preferably terminates between 1 cm. and 40 cm. proximal of the side port 309, or more preferably between 5 cm. and 30 cm., 10 cm. and 25 cm., or 15 cm. to 20 cm proximally of the side port.

The advantages of having the guidewire removing means 310 terminate proximally of the side port 309 are several. First, the catheter shaft 301 with the side port 309 is theoretically relatively weaker than a catheter shaft without the side port 309. Therefore, it is possible that if sufficient force were exerted on the catheter, the catheter could buckle at the side port 309. If the guidewire removing means 310 extends up to and into the side port 309, any such weakness in the catheter shaft 301 can be exacerbated. This problem is therefore limited by terminating the guidewire removing means 310 proximal of the side port 309.

Second, in the event that the catheter shaft 301 were to buckle, if the guidewire removing means 310 terminates proximal of the side port 309, the catheter shaft 301 has a higher probability of returning to its original shape. Accordingly, if a stylet, for example, is being used in conjunction with the catheter 300, there is less likelihood that the stylet tip could protrude out of the side port 309 or out of the guidewire removing means 310 and damage vessel structure or tissues.

Third, as mentioned, it is preferred that the guidewire removing means 310 terminates proximally of the side port 309. This has a tendency to position the guidewire removing means 310 outside of the coronary artery when in use. It is conceivable that when the guidewire removing means 310 that is not an inchoate slit is utilized that blood clotting can occur in conjunction with the guidewire removing means 310. However, by positioning the guidewire removing means 310 outside of the coronary artery, there is less of a probability that any clots, if formed, would cause damage to the coronary artery.

The uses of the catheter 300 of the present invention are the same as those illustrated in FIGS. 3 through 6.

In a preferred embodiment of the invention, the connector housing 318 is manufactured or adapted so that a guidewire extending through a channel in the connector housing and into and through the guidewire lumen may be removed laterally through the outer wall of the connector and the outer wall of the guidewire lumen. This feature allows rapid exchange of the catheter without the use of guidewire extensions. In FIGS. 33 and 34 a portion of the connector housing 318 is illustrated as removed. This section is referred to herein as the removable wall section 321. It will be appreciated that the catheter shaft 301 and the outer wall 315 of the guidewire lumen 316 is exposed. Accordingly, the guidewire removing means 310 are exposed and a guidewire extending through the guidewire lumen 316 can be removed laterally through the outer wall 315 in the guidewire lumen 316.

In FIG. 32, a guidewire 330 is shown extending through the guidewire lumen 316. In FIG. 33, the guidewire 330 is shown being moved laterally through the guidewire removing means 310 in the outer wall 315 of the guidewire lumen 316 and through the connector housing 318, where the portion of the connector housing 318 has been removed. In FIG. 34 the guidewire 330 is shown being removed from the guidewire lumen 316 to the termination point 311 of the guidewire removing means 310. Removal is accomplished by withdrawing the catheter 300 from the patient, while holding the guidewire 330 in substantially the same position. Thereafter, the catheter can be easily removed from the relatively short remaining section of the guidewire 330 that extends from the termination point 311 of the guidewire removing means 310 to the distal end 307 of the catheter without the need of an extension wire.

As will be appreciated, the removable wall section of the connector housing 318 operates to allow the lateral removal of the guidewire 330 from inside the connector housing 318 and into contact with the guidewire removing means 310 of the catheter shaft 301. Thereafter, the guidewire 330 is capable of lateral removal through the guidewire removing means 310 in the catheter shaft 301. Moreover, through the use of a complete connector housing 318, as opposed to a partial connector housing, there is less opportunity for premature removal of the guidewire from the guidewire lumen.

Figure 35:
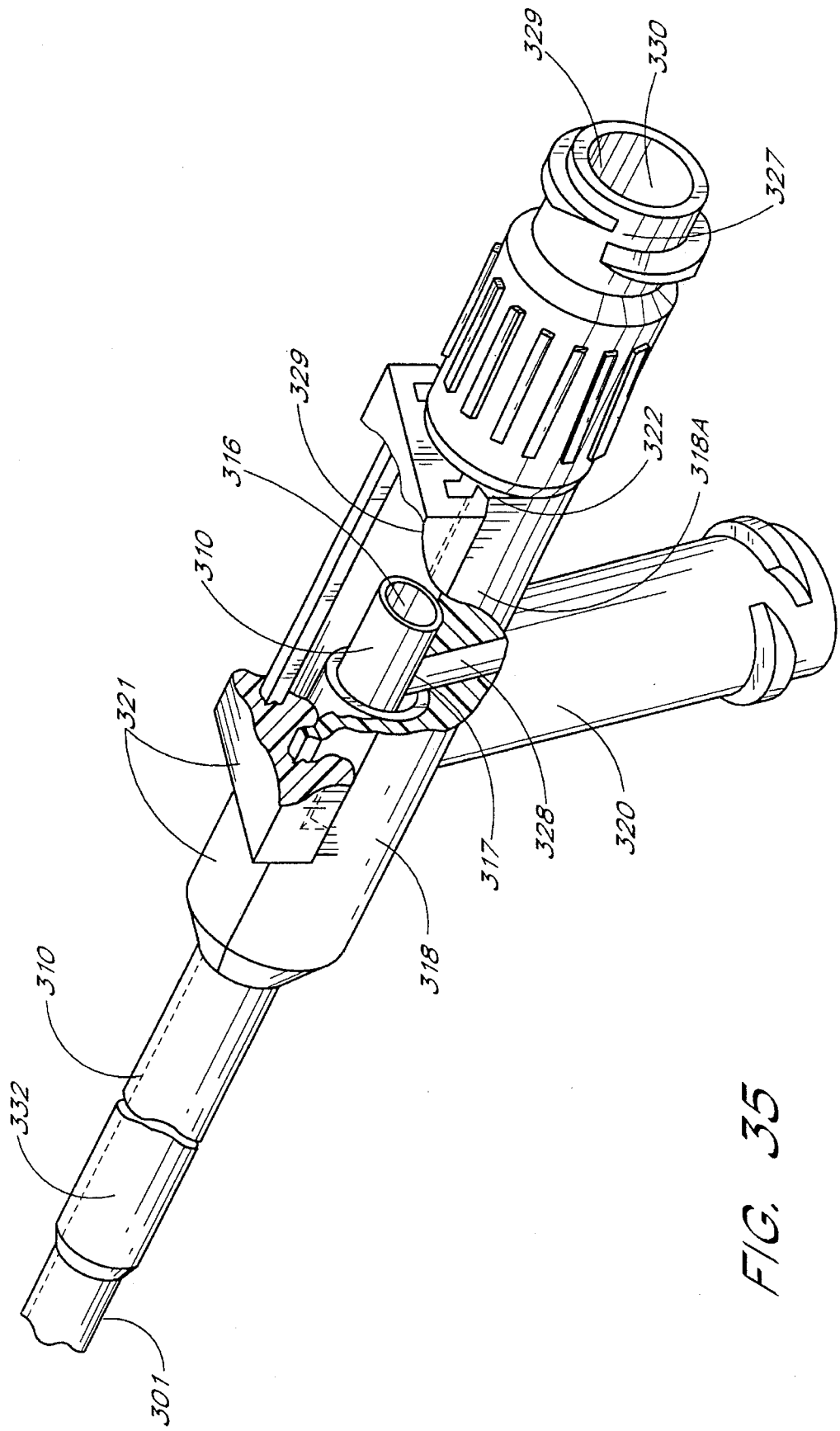
FIG. 35 is a cut-away side elevational view of a connector housing design in accordance with the present invention.

Accordingly, in accordance with another embodiment of the present invention, there is provided a connector having a removable wall section for use with the catheter. A preferred connector of the present invention is illustrated in FIG. 35, which is a cut-away side elevational view of a preferred connector housing 318 of the invention. The Figure illustrates the arrangement of the catheter shaft 301 in relation to the inflation channel 328 and a guidewire channel 329 in the connector housing 318. As will be observed, the guidewire channel is designed to direct a guidewire from its proximal opening into the proximal end of the guidewire lumen 316 of the catheter 300. The inflation channel 328 of the connector housing 318 is designed to communicate an inflation fluid from its proximal opening into the balloon inflation lumen 317 of the catheter 300 in its proximal end.

Accordingly, upon removal of the removable wall section 321, the guidewire removing means 310 in the catheter 300 is exposed and a guidewire can be removed from the proximal opening of the connector housing 318 and through the guidewire removing means 310 in the catheter shaft 301. In the illustrated embodiment, the removable wall section is maintained in position with a removable proximal end section 327 and a sliding rail assembly (each of which will be discussed below).

Figure 36:
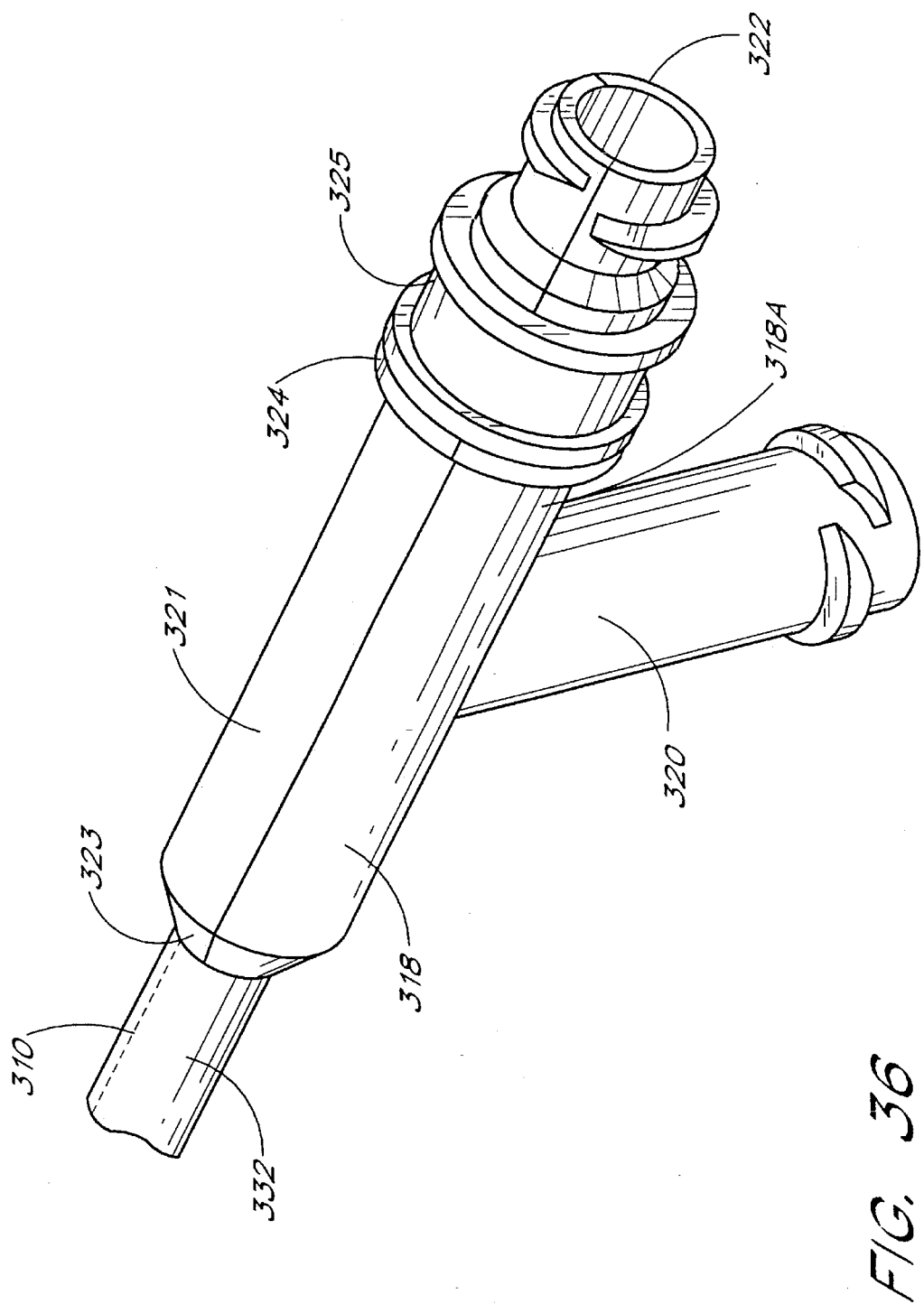
FIG. 36 is a side elevational view of an alternative design of the connector housing of the present invention.
Figure 37:
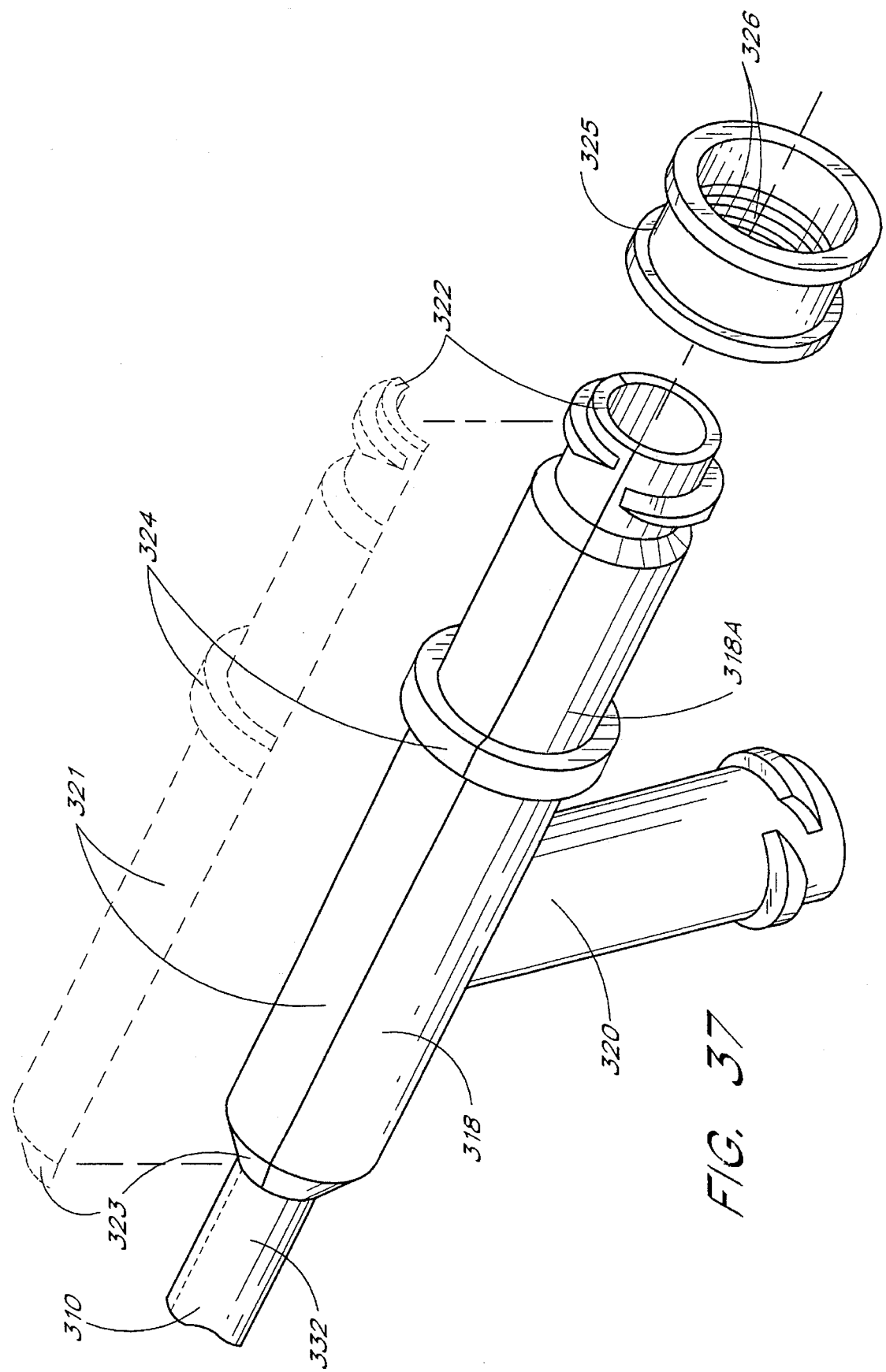
FIG. 37 is a partially exploded side elevational view of the connector housing in FIG. 36.

The maintenance of position of the removable wall section 321 can be accomplished in a variety of manners. For example, connector housing with a relatively simple removable wall section design is illustrated in FIGS. 36 and 37. There, a portion of the connector housing parallel and proximate to the guidewire lumen in the catheter shaft is removable, so as to expose the guidewire removing means underneath the removable wall section. When in place, the removable portion allows the user to torque the guidewire as necessary without fear that the guidewire will be forced from or open the guidewire removing means. However, when the removable portion is detached, the guidewire can be easily removed from the guidewire lumen through the guidewire removing means. Further, the removable portion, when being detached or when detached, does not interfere with the normal operation of the catheter, in particular, the connector section attached to the balloon inflation lumen.

This efficient mechanism for removing a guidewire is subject to a variety of additional embodiments that assure that there is not a premature release of the removable portion, yet facilitate removal when it is desired.

In FIG. 36, which is a side elevation view of a simple design of a connector meeting these requirements. A double-arm connector or connector housing 318 is mounted on the proximal portion of the catheter shaft 301. The connector housing 318 preferably has two arms which define channels through the connector housing 318. The first arm 318A extends from a proximal end 322 of the connector housing 318 to a distal end 323 of the connector housing 318 and is constructed to receive the catheter shaft 301.

The second or angled arm 320 is branched off of the connector housing 318. The channel in the first arm extends from the proximal end 322 to the distal end 323 of the connector housing 318. The channel in the angled arm 320 extends from the proximal end of the angled arm 320 and into the channel in the first arm 318A.

The connector housing 318 in the first arm 318A additionally comprises a removable wall section 321. The removable wall section 321 extends from the proximal end 322 of the connector housing 318 to the distal end 323. Essentially, the removable wall section 321 is a portion of the wall of the connector housing that is adapted or constructed to be removed by the operator of the catheter. Further, upon removal of the removable wall section 321, in a preferred embodiment, the guidewire removing means in the catheter shaft (not shown) should be exposed so that a guidewire can be laterally removed from the catheter shaft from the proximal opening of the catheter shaft to the termination point of the guidewire removing means. Accordingly, the removable wall section must be wide enough so that, upon its removal, a sufficient space is created that a guidewire can be easily pulled through.

In a preferred embodiment of the connector housing 318, this is accomplished by manufacturing the connector housing 318 so that the removable wall section is freely detachable from the connector housing. This may be accomplished by either manufacturing the connector housing in two parts or through cutting or separating the connector housing along two substantially parallel lines after manufacture.

To prevent premature removal of the removable wall section, a sealing member 325 (here shown as an annular ring) can be removably positioned on the proximal end 322 of the connector housing 318 to hold the removable wall section in place. The sealing member can have any geometry; however, an annular ring is preferred, because of its ease of manufacture and use. Internally on the sealing member 325, the sealing member preferably includes structure to make it more difficult to slide the sealing member off of the connector housing. For example, as shown in FIGS. 36 and 37, where as annular ring is used as the sealing member 325, it is preferable that it include circumferential ridges 326 on its interior to make it more difficult to remove from the connector housing 318. The sealing member 325 is removed axially from the guidewire.

Alternatively, the annular ring may comprise part or all of the connector housing 318, so that in use, the annular ring is removed proximally (axially) off of the guidewire, and then the guidewire is removed laterally out of the catheter, through guidewire removing means in the side of the catheter body and, as appropriate, through a longitudinal slot or removable wall section of the remaining portion (if any) of the connector housing 318.

The connector housing 318 can additionally comprise a stop block 324. The stop block 324 can be positioned on the removable wall section and/or the remainder of the connector housing to prevent the sealing member 325 from being pushed any further distally along the connector housing 318 toward the angled arm 320 than is necessary to hold the removable wall section in position.

In use, referring now to FIG. 37, the sealing member 325 is removed off the proximal end 322 of the connector housing 318 and the removable wall section 321 can be lifted freely from the connector housing 318 (shown in phantom). Upon removal of the removable wall section 321, the guidewire removing means 310 in the catheter shaft 301 is exposed and a guidewire can be removed therethrough.

Figure 38:
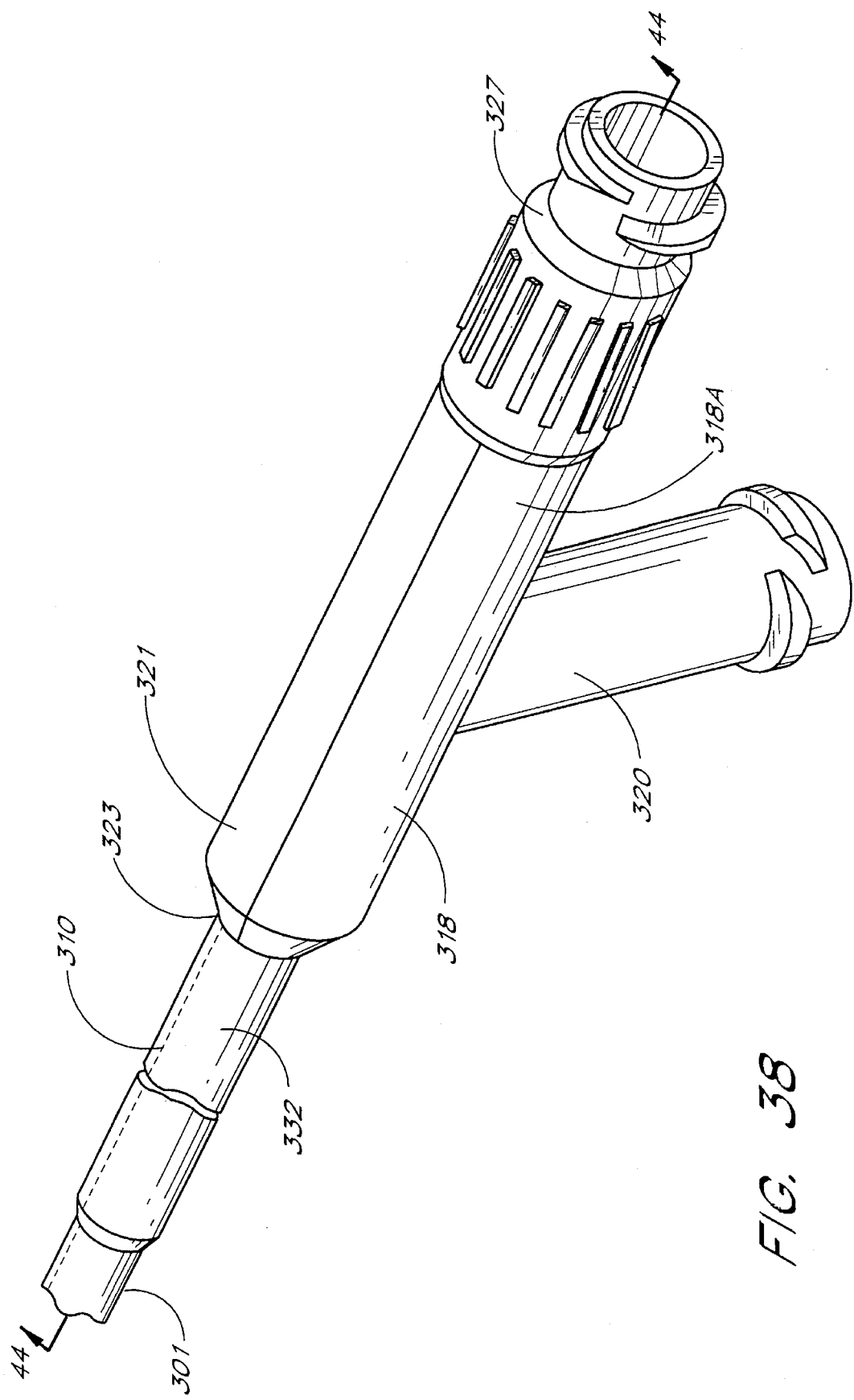
FIG. 38 is a side elevational view of another alternative design of the connector housing of the present invention.

Another embodiment of the connector housing of the present invention is shown in FIG. 38. In this embodiment, the operation of the sealing member and stop block of the embodiment shown in FIGS. 36–37 are combined in the removable proximal end 327. In FIG. 38, it will be seen that upon detachment of the removable proximal end 327, the removable wall section 321 can be freely removed. The removable proximal end 327 and the connector housing 318 can have complementary threading or other similar means to prevent premature removal of the removable wall section 321. For example, in the embodiment shown in FIG. 39 threading 382 is used. In this embodiment, the removable end piece is screwed off the connector housing 318, and thereafter, the removable wall section 321 is detached from the connector housing 318.

Figure 40:
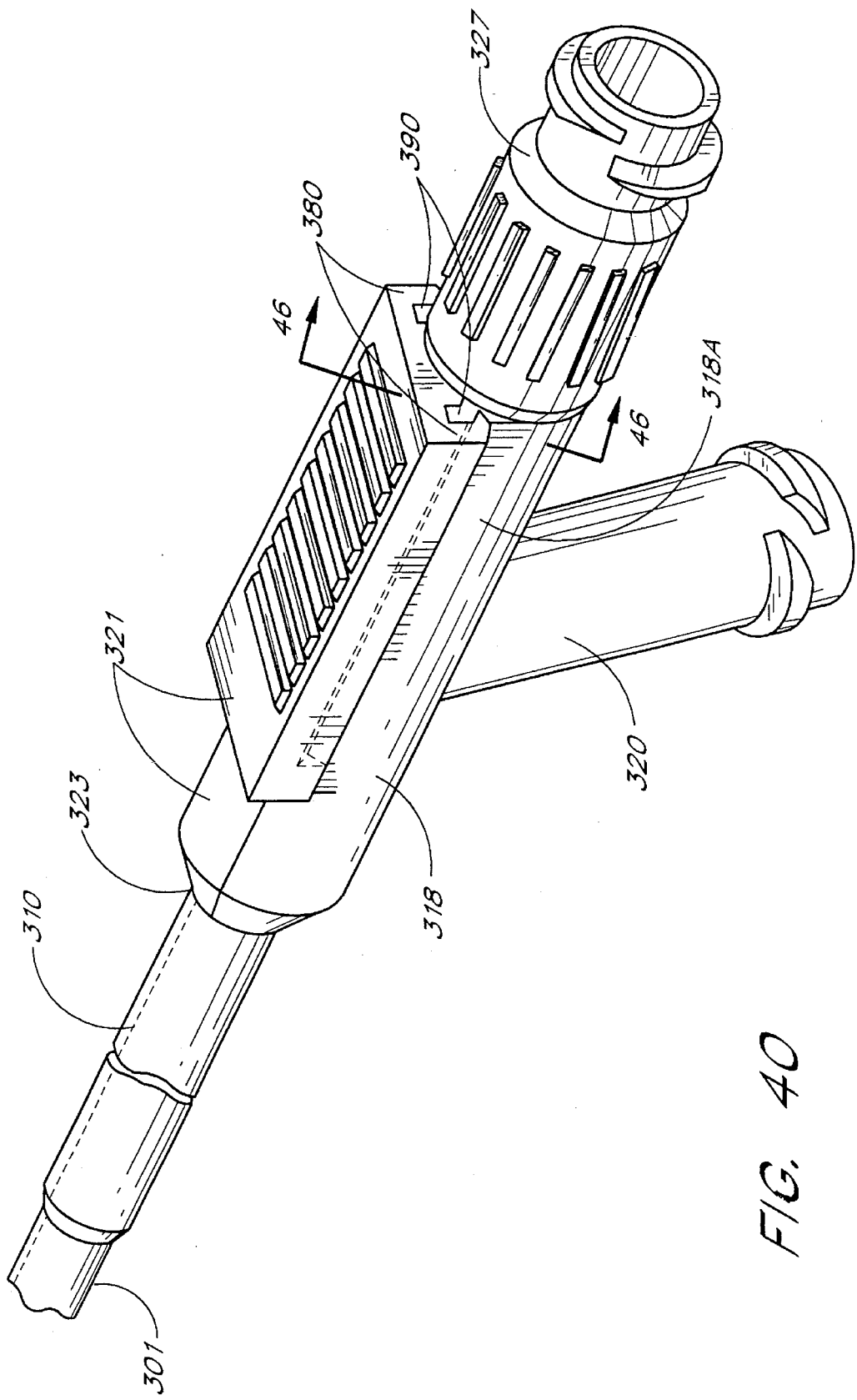
FIG. 40 is a side elevational view of yet another alternative design of the connector housing of the present invention.
Figure 41:
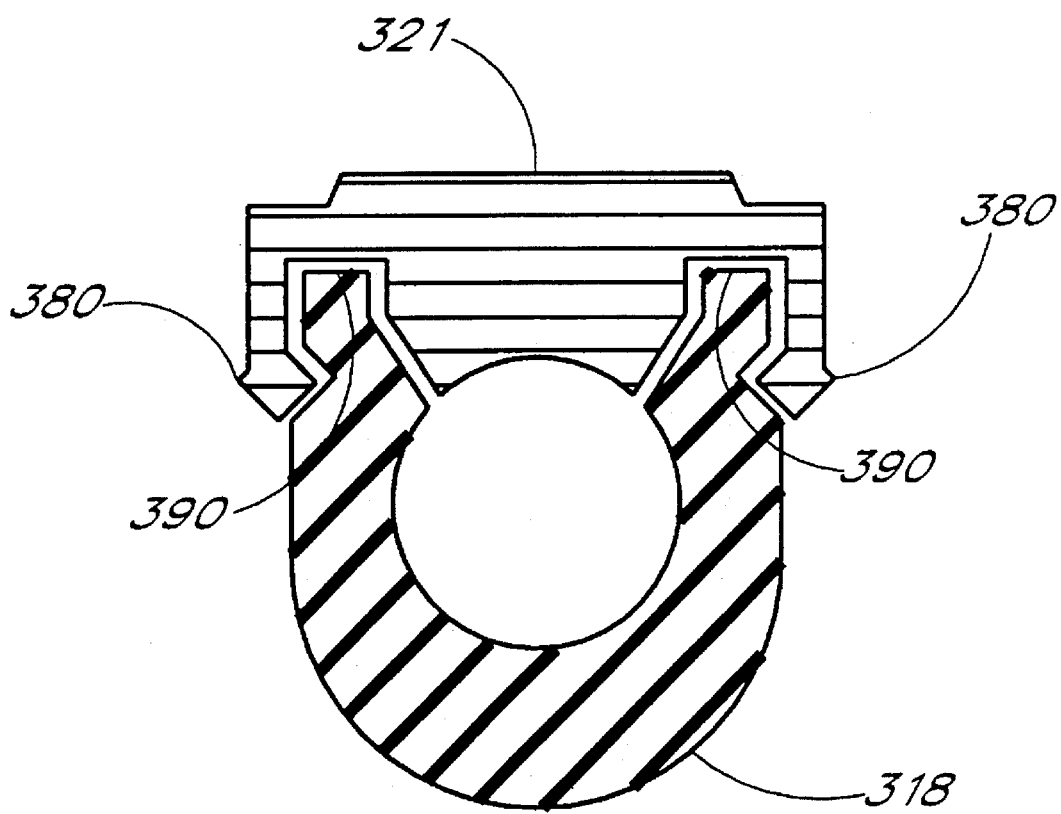
FIG. 41 is a transverse cross sectional view of the connector housing in FIG. 40 taken along line 46—46.
Figure 42:
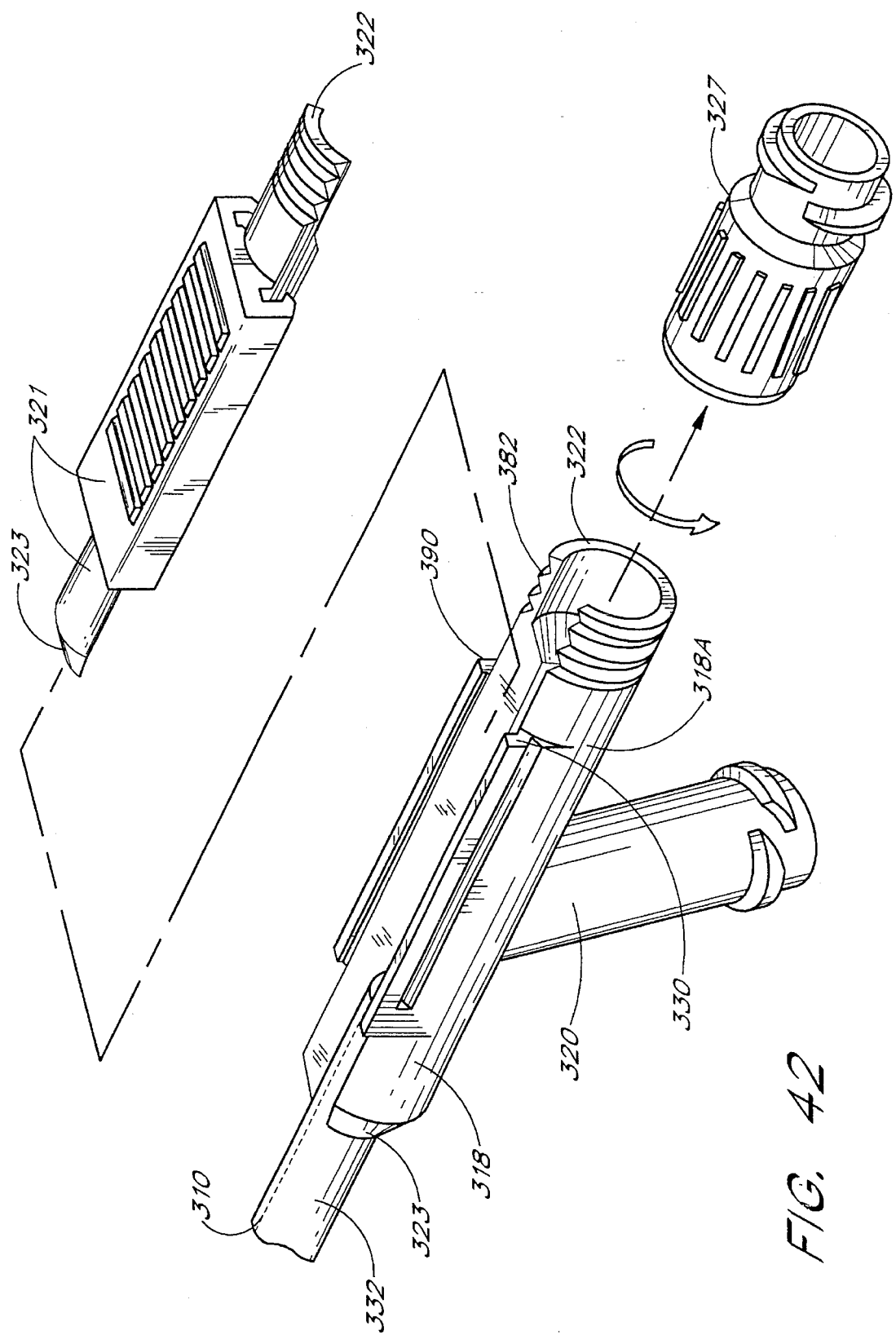
FIG. 42 is a partially exploded side elevational view of the connector housing in FIG. 40.

Still another embodiment of the connector housing of the present invention is shown in FIG. 40. This embodiment preferably utilizes the removable proximal end embodiment shown in FIGS. 38 and 39 and additionally comprises mounting the removable wall section 321 on complementary sliding tracks 380, 390. The design of the complementary sliding tracks are also shown in transverse cross sectional view in FIG. 41. In FIG. 42, it will be seen that removal of the removable wall section is initially longitudinal as the operator slides the removable wall section 321, proximally, prior to detachment of the tracks, at which time, the removable wall section 321 can be pulled laterally away.

Figure 43:
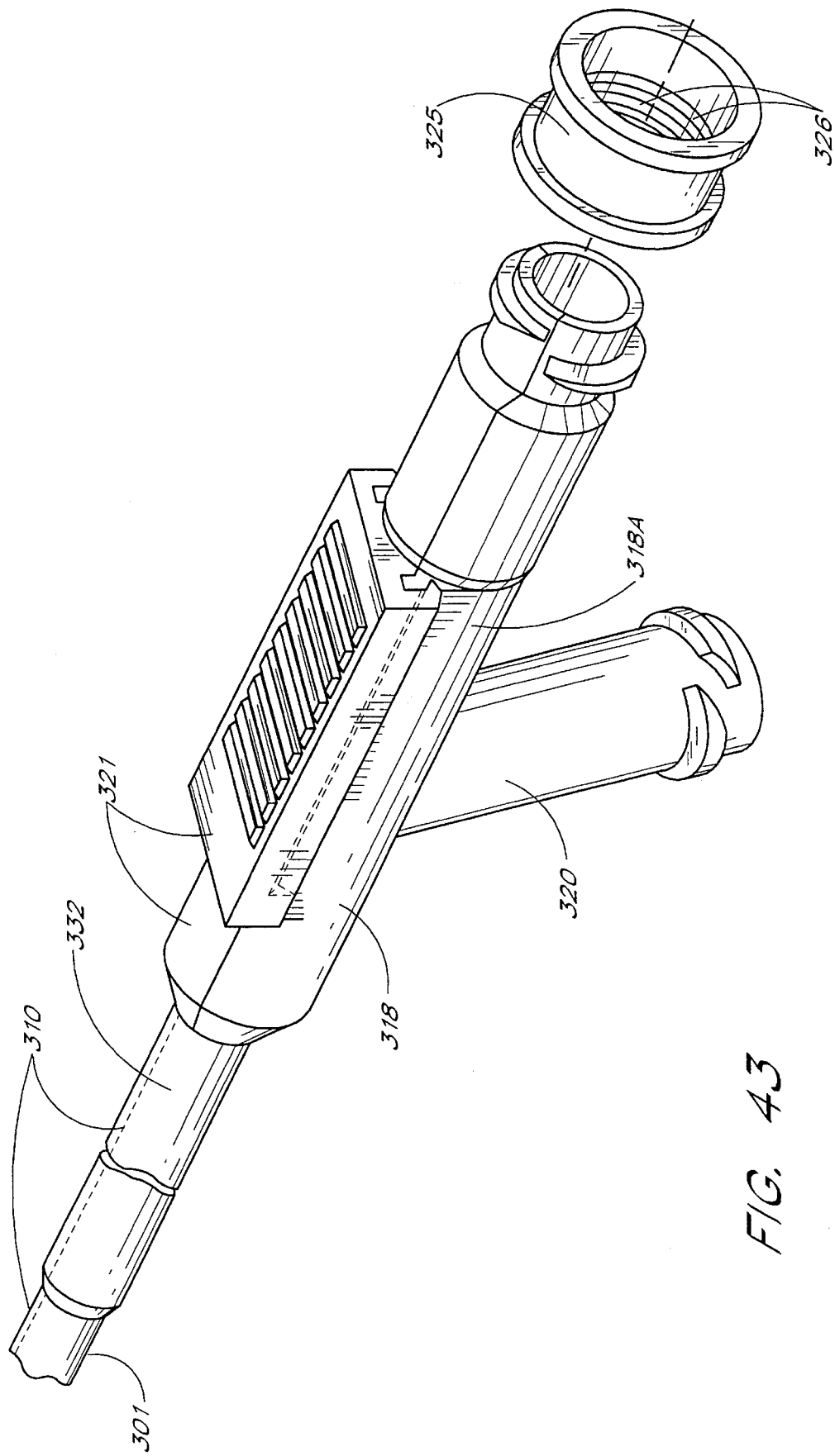
FIG. 43 is a side elevational view of yet another alternative design of the connector housing of the present invention.

As shown in FIG. 43, instead of the removable proximal end 327 as shown in FIGS. 36–37, a sealing member 325 can alternately be used, as described previously.

In each of the embodiments described in FIGS. 32–43, it is possible to reattach the removable wall section 321 after it is removed. Accordingly, conversion from over-the-wire mode to rapid-exchange mode is now possible. It will be appreciated that a catheter of the invention can be (i) inserted into a patient in over-the-wire mode, (ii) the removable wall section removed, and (iii) the guidewire removed through the guidewire removing means and the catheter removed from the patient in a rapid-exchange manner without the need for a guidewire extension and can be performed by a single operator. Thereafter, a second catheter can be inserted into the patient in rapid-exchange mode (with the guidewire extending from the distal end of the catheter and out the side port). Once the catheter is positioned in the patient, the guidewire can be removed and reinserted into the patient in over-the-wire mode.

METHODS OF USING THE CATHETER

The catheter of the present invention may be used as a rapid exchange catheter with the guidewire 50, 252 extending through the side port 34, 234 and out of the distal end 16, 216 of the guidewire lumen 20, 220. Alternatively, it may be used as a conventional over the wire catheter with the guidewire 50, 252 extending substantially the entire length of the catheter shaft 12, 212 from the proximal end (either through a "Y" connector 62, 80, or 242 or through the proximal opening 32, 232) distally through the entire length of the catheter shaft and out of the distal end thereof.

A revolutionary aspect of the catheter of the present invention is that it may readily and rapidly be converted from one mode of use to the other. Thus, it can be used first as a rapid exchange catheter, with the guidewire extending in the guidewire lumen 20, 220 only from the side port 34, 234 to the distal end of the catheter. It can be converted from this rapid exchange mode of use to conventional over-the-wire use simply by removing the guidewire and, while maintaining the catheter 10, 210 in place in the patient, inserting a new guidewire 50, 252 into the proximal end of the guidewire lumen 20, 220 (through a "Y" connector or through the proximal opening 32, 232) and extending the guidewire 50, 252 out of the distal end of the catheter.

When the catheter of FIGS. 1–6 is being used as a conventional over the wire catheter, it can be converted into a rapid exchange catheter by removing the removable "Y" connector 62 (if used), and, with the guidewire extending proximally out of the proximal opening 32, maintaining the guidewire 50 in position in the patient while moving the guidewire laterally out of the outside wall 30 of the guidewire lumen 20 through the guidewire removing means 40 and simultaneously withdrawing the catheter 10 proximally until the distal end 16 of the catheter 10 is outside of the patient. During this portion of the procedure, the guidewire 50 is held by grasping it at the proximal end. Then the operator may hold the guidewire 50 by grasping the portion of the guidewire 50 exposed at the distal end 16 of the catheter 10, remove the catheter 10 off of the proximal end of the guidewire 50, and insert a new catheter 10 over the guidewire 50 while maintaining the position of the guidewire 50 in the patient. The insertion of the new catheter 10 may be accomplished in rapid exchange mode by retrograde insertion of the proximal end of the guidewire 50 through the distal end of the catheter and out of the sideport 34. The proximal end of the guidewire is then held while the catheter 10 is advanced back into position in the patient. The catheter can then be used as a rapid exchange catheter. Alternatively, if desired, the guidewire 50 may be removed with the catheter maintained in position, and in a matter of seconds the guidewire may be reinserted through the proximal opening 32 or through the proximal end 14 of the catheter shaft 12 to convert the mode of use to conventional over the wire use.

Thus, it will be appreciated that the catheter of the present invention can easily be used in either a rapid exchange mode or an over the wire mode; that conversion between modes of use may be readily accomplished; that guidewire exchange may be accomplished in either mode of use, and that catheter exchange when in either mode of use can be accomplished without use of an extension guidewire; and that all of the forgoing conversions and modes of use can be accomplished while maintaining the positioning of either the guidewire or the catheter in the patient.

Thus, one method of the present invention comprises inserting the catheter of FIGS. 1–6 into the patient with the guidewire 50 going through the proximal opening 32 and extending from that point distally through the entire remaining length of the catheter shaft 12 and out of the distal end 16. The guidewire 50 can then be exchanged by removing it and reinserting it through the proximal opening 32. The catheter can be exchanged by holding the guidewire as explained above while peeling away the catheter laterally while withdrawing it so that the guidewire is pulled through the guidewire removing means 40 until the distal end of the catheter is outside the patient. The guidewire is then held distally of the catheter and a new catheter is inserted, this time in rapid exchange mode. Once that catheter is in place, the guidewire can be rapidly exchanged (if desired) to convert the catheter back into the over-the-wire mode of use as explained above.

In another method of use, the catheter of FIG. 6 can be used. This catheter can be used with the guidewire in the side port or the proximal opening, as explained above, with the same catheter and guidewire exchanges possible. Moreover, it can be used with the guidewire extending through the entire length of the guidewire lumen 20 through the guidewire adapter 64. Exchange of the guidewire from the guidewire adapter 64 to the proximal opening 32 and vice versa is also contemplated.

The identical modes of use explained in connection with the FIGS. 1–6 catheter can be used with the removable or severable "Y" connector catheter of FIGS. 7–31, except the guidewire passes simultaneously through the proximal opening 32, 232 and the guidewire adapter 64, 240 of the "Y" connector 80, 242. Further, in these modes of use, the conversion from over-the-wire use to rapid exchange use will require removal of the removable "Y" connector 80 or removal a portion of the breakaway "Y" connector 242 (or other provision of a longitudinal slot or passageway through the "Y" connector) prior to and in addition to use of the guidewire removing means 40, 250.

Thus, for example, the catheter 210 of FIGS. 16–31 can be first inserted in over the wire mode, with the guidewire 252 extending from the proximal opening 232 through the guidewire connector 240 and distally through the guidewire lumen 220, through the balloon 224, and out of the distal end 216 of the catheter. In this configuration, the catheter is inserted into the patient and positioned in the conventional manner. The guidewire 252 is exchanged simply by maintaining the positioning of the catheter 210 in the patient, withdrawing the guidewire out of the proximal end 214 of the guidewire connector 240, and inserting another guidewire 252. If exchange of the catheter 210 is necessary, the breakaway piece 246 of the "Y" connector 242 is removed, the guidewire is removed laterally out of the "Y" connector 242 beginning at the proximal end of the connector 242, and then the guidewire 252 is held securely in position while the catheter is withdrawn from the patient, simultaneously pulling the guidewire 252 laterally out of the guidewire lumen 220 through the guidewire removing means 250. Where a tear-away strip 266 comprises the guidewire removing means 250, the strip 266 is pulled off while the catheter 210 is pulled out of the patient. When the distal end 216 of the catheter 210 is out of the patient and the guidewire 252 is exposed at the distal end 216, then the guidewire is grasped distally of the catheter 210 and the catheter 210 is removed off of the proximal end of the guidewire 252. Next, a new catheter 210 is threaded onto the guidewire by inserting the guidewire into the distal end of the guidewire lumen 220, proximally through the guidewire lumen 220 to the side port 234, and out of the side port 234. The catheter 210 is then advanced into the patient over the guidewire 252 while holding the guidewire 252 securely in position. If desired, the guidewire 252 can then be removed while holding the catheter 210 in position, and reinserted through the proximal end 214 of the guidewire lumen 220 through the entire length of the catheter 210, to convert back to over the wire mode.

As will be appreciated, where a reattachable removable wall section is used on a connector housing in accordance with the present invention, for example, in the embodiments discussed in connection with FIGS. 35–43, a single catheter can be used consecutively in over-the-wire mode and rapid-exchange mode, in either order. This mode of operation is illustrated schematically in FIGS. 44A through 44d.

Figure 44A:
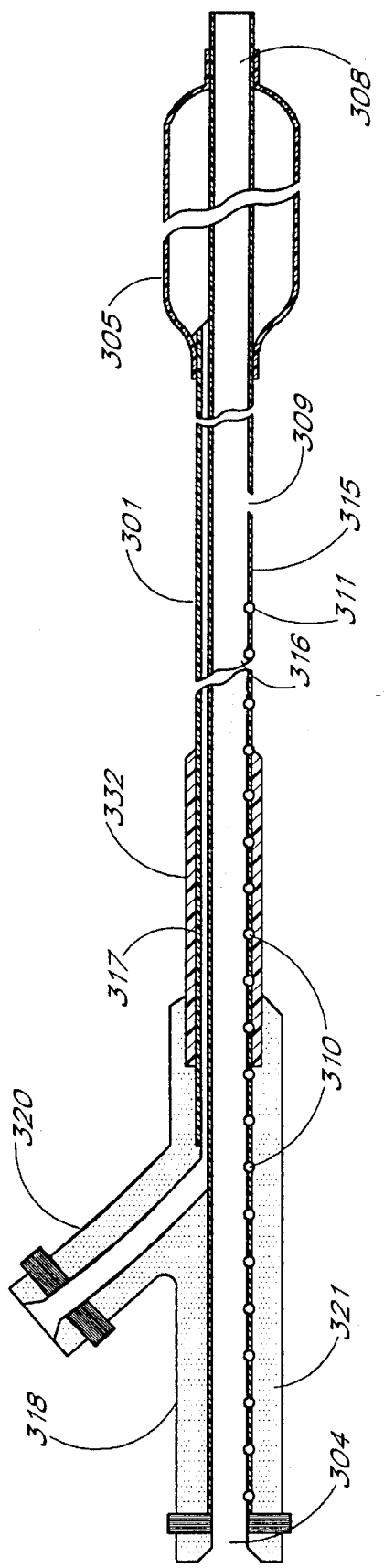
FIGS. 44a through 44d is a series of cross sectional views showing conversion from over-the-wire mode to rapid-exchange mode and back to over-the-wire mode.

In FIG. 44A, a catheter of the present invention is shown schematically in a longitudinal cross sectional view. The catheter 300 has a shaft 301 with an outer wall 315 and a guidewire lumen 316 extending from the proximal end 303 to the distal end 307. The outer wall 315 additionally comprises guidewire removing means, indicated by dotted line 310, extending from the proximal opening of the guidewire lumen distally toward the balloon 305, adapted for removal of a guidewire laterally through the outer wall 315. The outer wall 315 also comprises a side port 309, being adapted for insertion of a guidewire therethrough. An angioplasty balloon 305 is mounted on the distal portion. The balloon 305 is in operative communication with a balloon inflation lumen 317 that extends from a side arm 320 in a connector housing 318 and terminates in the balloon 305. The connector housing 318 is mounted on the proximal end 303. The connector has a removable wall section 321 that is detachable and reattachable as discussed in connection with FIGS. 35–43.

Figure 44B:
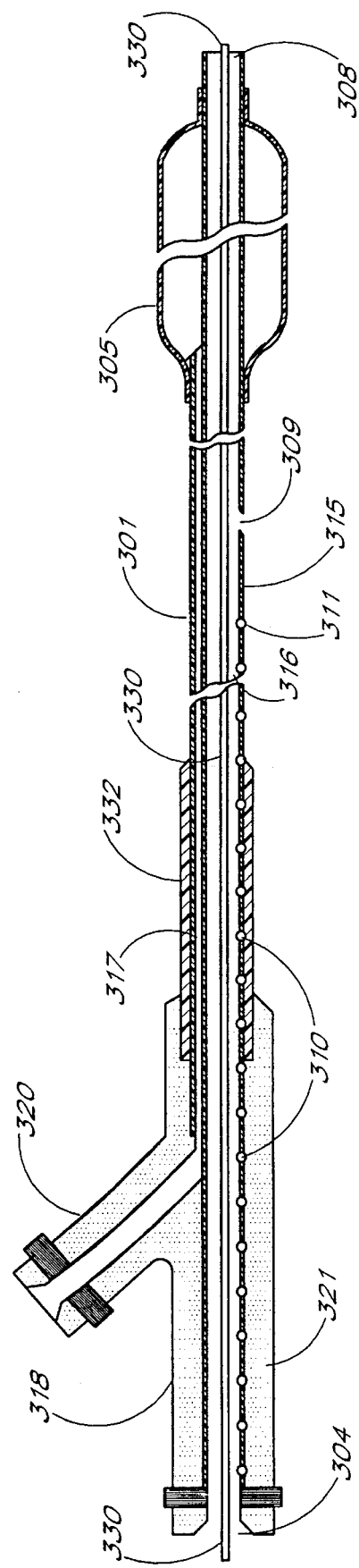
Figure 44C:
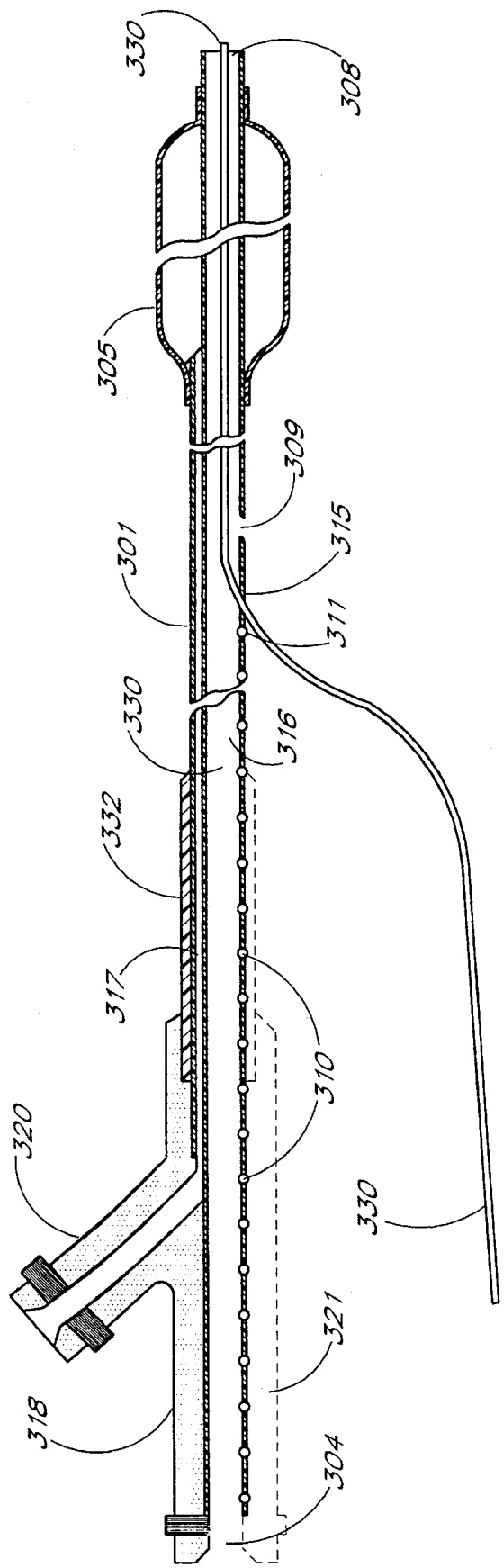
Figure 44D:
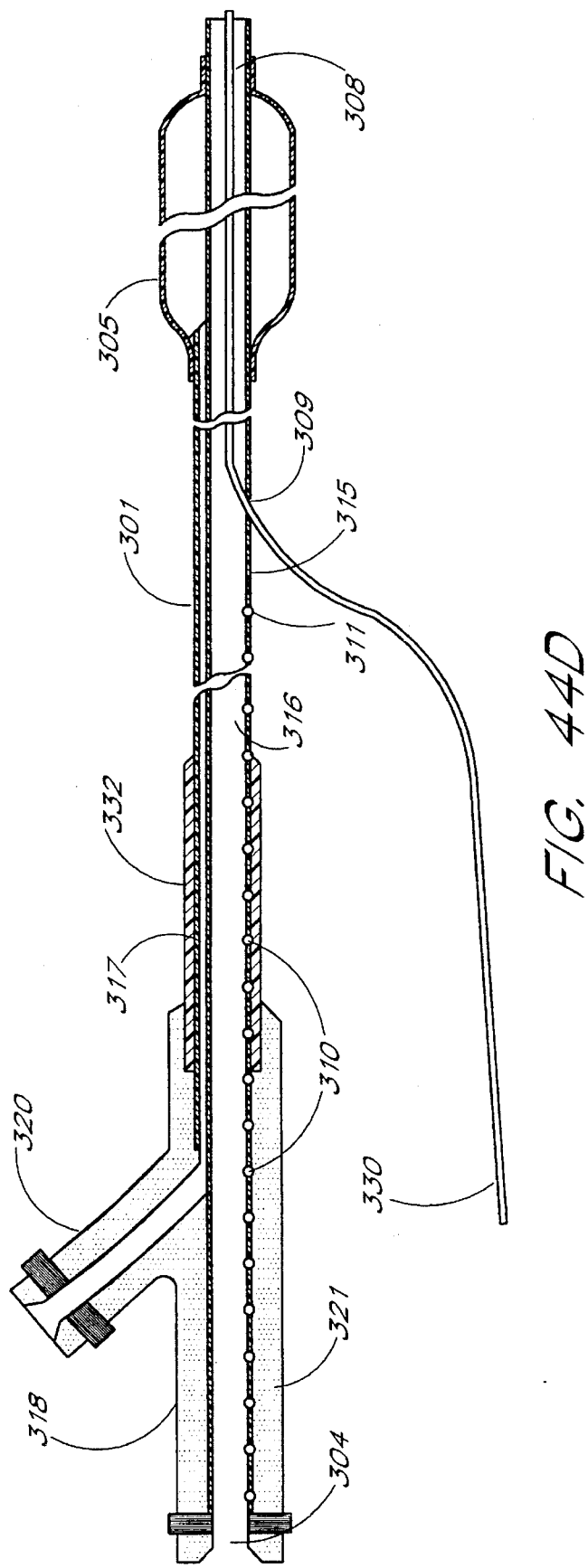

In FIG. 44b, a guidewire 330 is positioned in the guidewire lumen 316. Assuming catheter exchange is required, the removable wall section 321 is removed and the guidewire 330 is removed through the guidewire removing means 310, as shown in FIG. 44c. Thereafter, the catheter 300 is removed from the guidewire 330, without the need for an extension wire. Once the catheter is removed, a distal end of the guidewire remains positioned at, for example, the stenosis, and a new catheter can be inserted in rapid-exchange mode in a new or the same catheter in which the removable wall section is remounted. See FIG. 44d. Once the catheter is positioned in, for example, a stenosis, the guidewire can be withdrawn and reinserted in over-the-wire mode. See FIG. 44b.

As will be appreciated, when the catheter is in over-the-wire mode, the guidewire acts to enhance the pushability and torqueability (herein, "stiffness") of the catheter shaft. When operating in rapid-exchange mode, the guidewire is outside of the catheter shaft along a substantial portion of its length. Therefore, it is often desirable to enhance the stiffness of the catheter shaft. In accordance with a preferred embodiment of the present invention, a stylet is inserted into the guidewire lumen of the catheter shaft in order to achieve enhanced stiffness.

Typically, a stylet for use in the present invention is an elongate solid or tubular member that is sized to fit relatively snugly within the guidewire lumen. Conventionally, such stylets are formed from metals or extruded plastic materials. Preferred stylets for use in the invention additionally include a taper in a distal portion of the stylet and, typically, the stylet terminates on its distal end with a rounded tip to make the stylet less dangerous to vessel tissues and/or less likely to damage the guidewire lumen of the catheter.

Figure 45:
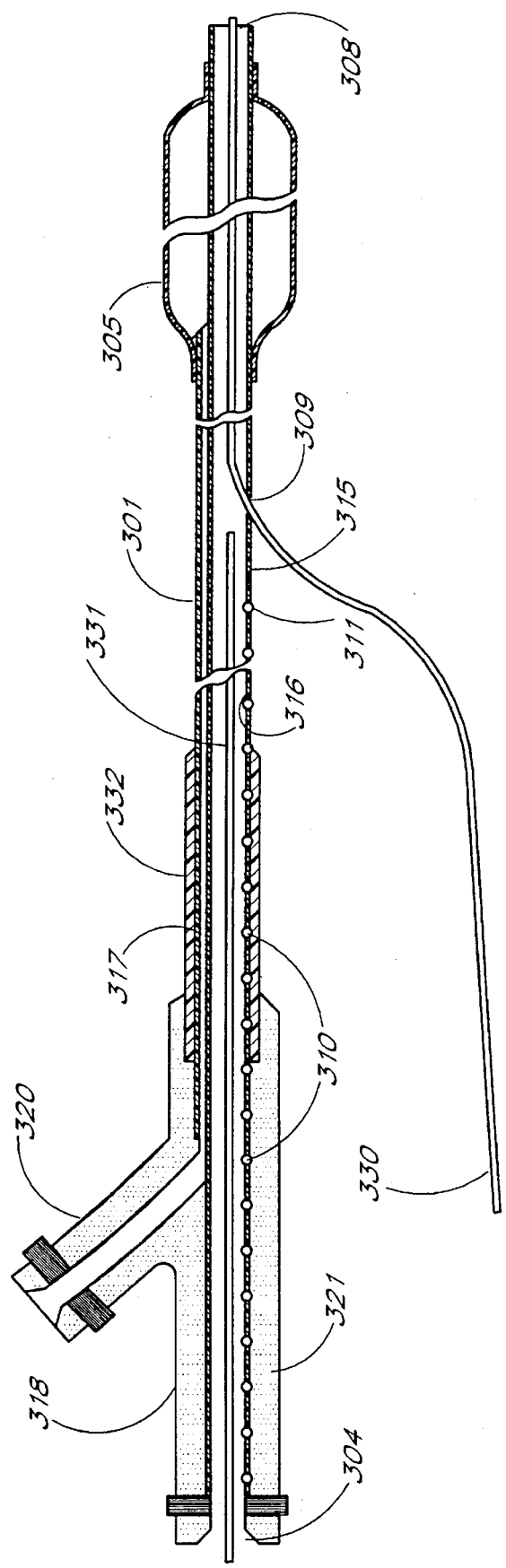
FIG. 45 is a longitudinal cross sectional view of a catheter in accordance with the invention being operated in rapid-exchange mode with a stylet inserted in the guidewire lumen.

An embodiment of the invention employing a stylet is illustrated in FIG. 45 which is a longitudinal cross sectional view of a catheter in accordance with the invention being operated in rapid-exchange mode with a stylet inserted in the guidewire lumen.

As will be seen, the catheter 300 has the same features as the catheters discussed in FIGS. 32–34. Typically, an operator will insert the stylet 331 into the proximal opening 304 of the guidewire lumen 316 and slide the distal end of the stylet 331 distally toward the side port 309. Preferably the distal end of of the stylet 331 is positioned proximal and adjacent to the side port 309. However, the distal end of the stylet 331 may be positioned wherever sufficient stiffness is achieved allowing the user adequate push and torque.

The positioning of the stylet 331 may be accomplished either before, after, or during the insertion of a proximal end of the guidewire 330 in through the distal opening 308 of the catheter shaft 301 and through the guidewire lumen 316 and out through the side port 309, i.e., placing the catheter in rapid-exchange mode.

When it is desired to revert back to over-the-wire mode, the guidewire 330 and the stylet 331 may be simply removed and the guidewire 330 threaded in through the proximal opening 304 through the guidewire lumen 316 and out the distal opening 308. Alternatively, the catheter 300 could simply be removed, leaving the guidewire 330 in place, and a new catheter inserted in rapid-exchange mode.

In one preferred embodiment, when the guidewire is removed from the connector and/or the guidewire removing means in the catheter shaft, the guidewire is held relatively straight, and the connector and/or the catheter shaft is peeled laterally away from the guidewire.

Although the present invention has been described in the context of certain preferred embodiments, it is intended that the scope of the present patent be measured with reference to the appended claims and any equivalents thereof.

What is claimed is:

1. A multi-lumen vascular catheter which allows the exchange of a guidewire or catheter while the catheter is positioned within a patient's vasculature, comprising:

an elongate, flexible catheter shaft having a proximal end and a distal end and having at least a first and a second lumen extending distally from said proximal end, each of said lumens having a proximal and a distal opening, wherein said catheter further includes guidewire removing means in the outside wall of the first lumen extending distally from the proximal opening for permitting a guidewire extending through said first lumen to be moved laterally from said first lumen through the outside wall of the first lumen; and a first connector near the proximal end of said catheter, said connector encircling said catheter shaft and having a first open, hollow channel in communication with the proximal opening of said first lumen, said connector including means for separating said connector longitudinally and moving a portion of said connector that is distinct from but juxtaposed with said guidewire removing means laterally away from said catheter shaft, to permit a guidewire extending longitudinally through said first channel into said first lumen to be moved laterally out of said first channel of said connector and out of the first lumen of said catheter.

2. The catheter of claim 1, wherein said first connector separates completely into first and second parts.

3. The catheter of claim 1, further comprising a second connector near the proximal end of said catheter having a second channel extending therethrough, said second channel communicating with the interior of the second lumen.

4. The catheter of claim 3, wherein said second connector is located distally of said first connector.

5. The catheter of claim 3, wherein said second connector is located proximally of said first connector.

6. The catheter of claim 5, wherein said first and second connectors are joined together in the form of a "Y".

7. The catheter of claim 3, wherein said first and second connectors are joined together in the form of a "Y".

8. The catheter of claim 1, further comprising an angioplasty balloon located at the distal end of the catheter, said balloon being in fluid communication with said second lumen for inflation and deflation of said balloon.

9. The catheter of claim 1, wherein said guidewire removing means is a slit.

10. The catheter of claim 1, wherein said guidewire removing means is continuous from the proximal opening of said first lumen to a point at least about 40 cm from the proximal end of said catheter shaft.

11. The catheter of claim 1, wherein said guidewire removing means is discontinuous, forming a perforated line from the proximal opening of said first lumen to a point at least 40 cm from the proximal end of said catheter shaft.

12. The catheter of claim 1, wherein said guidewire removing means is a relatively weak area of the wall of the first lumen.

13. The catheter of claim 12, wherein said weak area comprises a pair of juxtaposed grooves, one on the inside and the other on the outside of the wall of the first lumen.

14. The catheter of claim 1, wherein said guidewire removing means is a removable strip in a portion of the outside wall of the first lumen.

15. The catheter of claim 1, further comprising a permanently formed side port located within about 80 cm of said distal end, said side port extending through the outside wall of the first lumen and being large enough to permit insertion of a guidewire therethrough.

16. The catheter of claim 15, wherein said guidewire removing means extends from the proximal end of the catheter shaft to a point proximal of the side port.

17. The catheter of claim 16, wherein said point is between about 0.1 cm and 40 cm proximal of the side port.

18. The catheter of claim 15, wherein said side port is adapted to permit a guidewire to pass through said side port and through the portion of the first lumen distal to said side port, but is adapted to prevent a guidewire in the portion of the first lumen proximal to the side port from passing out of said lumen through the side port.

19. An angioplasty balloon catheter, comprising:

a catheter shaft with a proximal end and a distal end and having a first lumen extending therethrough, said first lumen having an outside wall and being of sufficient dimension to receive a guidewire extending through said first lumen, and an inflatable balloon positioned on the distal end;

a balloon inflation lumen extending through said shaft and in communication with said balloon;

a guidewire connector attached to the proximal end of said catheter communicating with said first lumen in such a manner as to direct said guidewire into said first lumen, said connector further having a wall; and means for permitting said guidewire, when extending through said first laterally removed through the wall of the connector and separate means for permitting said guidewire, when extending through said first lumen, to be removed through the outside wall of said first lumen while maintaining the longitudinal positioning of a guidewire in a patient, said means initially providing an enclosed first lumen in said connector prior to the removal of a guidewire therethrough.

20. The catheter of claim 19, wherein said guidewire connector is at least partially removable from said catheter shaft.

21. The catheter of claim 20, wherein upon separation of said segments, at least one of said segments is completely removable from said catheter shaft.

22. The catheter of claim 19, wherein the guidewire connector comprises a first portion that can be laterally removed away from the first lumen and a second portion that remains on the catheter shaft when said first portion is removed.

23. An angioplasty catheter that is convertible to and from over-the-wire mode to rapid-exchange mode, comprising:

a catheter shaft with a proximal opening in a proximal end and a distal opening in a distal end and having a first lumen extending therethrough, said first lumen having an outside wall and being of sufficient dimension to receive a guidewire and guidewire removing means formed in said outside wall of the first lumen for allowing said guidewire extending through said first lumen to be removed laterally through the outside wall, and a permanently formed side port located within about 80 cm of the distal end, said side port extending through the outside wall of the first lumen for permitting insertion of said guidewire therethrough, wherein said guidewire removing means terminates at a point proximal of the side port;

an inflatable balloon mounted near the distal end of the catheter shaft in communication with a balloon inflation lumen extending through said shaft;

a dual arm connector mounted near the proximal end of said shaft, said connector having first and second arms, said first arm forming a first channel encircling the catheter shaft and having an outside wall and a proximal opening, said first channel connected to said first lumen so that a guidewire can be inserted through the proximal opening of the first channel and into the first lumen of the catheter, and said second arm forming a second channel having an outside wall and a proximal opening in communication with the balloon inflation lumen;

said connector further comprising a removable wall section having a width in said outside wall of said first channel that is reversibly and completely disengageable from said connector, wherein, the width of the removable wall section is sufficient to permit said guidewire extending through the first channel to be laterally removed from the first channel, and, wherein, upon disengagement of said removable wall section the catheter is no longer encircled by the connector housing and so as to expose the guidewire removing means in the catheter shaft and said guidewire extending from the proximal opening of the first channel and into the first lumen can be removed laterally out of the connector and out of the catheter through the guidewire removing means; and means disengageably mounted on said connector housing to prevent disengagement of the removable wall section, said means being further operable to reengage said removable wall section, following disengagement.

24. The catheter of claim 23, wherein the first channel has a circumference and the removable wall section comprises a circumferential sector large enough to allow removal of a guidewire therethrough upon detachment of the removable wall section.

25. The catheter of claim 24, wherein the circumferential sector encompasses an angle between 15 and 180 degrees of the circumference of the first channel.

26. The catheter of claim 23, wherein the disengageable means comprises a detachable ring.

27. The catheter of claim 23, wherein the disengageable means comprises a detachable ring mounted on a proximal end of the first channel.

28. The catheter of claim 27, wherein the proximal end of the first channel additionally comprises threading and the detachable ring is secured thereon.

29. The catheter of claim 23, wherein means to reengage said removable wall comprises longitudinal recesses constructed in the first channel for receiving the removable wall section.

30. The catheter of claim 23, wherein the guidewire removing means terminates distally between about 0.1 cm and 40 cm proximal of the side port.

31. A "Y" connector and guidewire combination for use on a catheter shaft, comprising:

a connector body having a proximal end and a distal end and having a wall with a first side and a second side;

the connector body comprising a first channel extending from the proximal end to the distal end;

a guidewire extending through said first channel:

a removable longitudinal section of said first said of said wall, wherein removal of said section exposes said first channel;

the connector body further comprising a second channel formed in the second side of the connector body; and wherein the distal end of the first channel of the connector body includes means for mounting said connector body on a catheter shaft having a first and second lumen such that the proximal end of the first channel can direct said guidewire into the first lumen of the catheter and the second channel is in communication with the second lumen of the catheter.

32. A method for use in vascular catheterization of a patient, comprising:

positioning a catheter shaft having a proximal end and a distal end in the cardiac vasculature of a patient in an over-the-wire mode with a guidewire having a proximal and distal end extending through a first channel of a proximal connector mounted on the catheter and through the catheter shaft with the distal end of the guidewire extending from the distal end of the catheter;

removing a portion of the proximal connector to expose the first channel;

removing the guidewire from the first channel and laterally out of the catheter shaft through guidewire removing means extending distally along a majority of the length of the catheter while maintaining the positioning of the guidewire in the patient; and simultaneously sliding the catheter shaft proximally off of the guidewire;

inserting the proximal end of the guidewire into the distal end of a second catheter and out through a port in the side of said second catheter located within about 80 cm proximal of a balloon positioned on the distal end of said second catheter; and inserting said second catheter into said patient over said guidewire while maintaining the position of the guidewire in the patient.

33. The method of claim 32, comprising the additional steps of:

withdrawing the guidewire from the second catheter and from the patient; and then inserting the guidewire into the proximal end of the second catheter, and out of the distal end of the second catheter in the patient.

34. A vascular catheter, comprising;

a catheter shaft having a proximal end and a distal end and a guidewire lumen extending therethrough from a proximal opening to a distal opening;

a first guidewire removing means for permitting a guidewire to be removed laterally from said guidewire lumen extending from said proximal opening distally along a majority of the length of the catheter shaft;

a side port communicating with the guidewire lumen for insertion of a guidewire therethrough, said side port located distally of and separated from said first guidewire removing means; and a guidewire extending through said side port into said guidewire lumen and distally out of said distal opening.

35. The catheter of claim 34, wherein said side port is located within 0.1 and 60 cm distally of said first guidewire removing means.

36. The catheter of claim 34, further comprising a stylet in the portion of said guidewire lumen not occupied by said guidewire.

37. The catheter of claim 34, further comprising:

a guidewire connector on said catheter shaft having an access channel communicating with said proximal opening.

38. The catheter of claim 37, wherein at least a portion of said guidewire connector is removable proximally off of said guidewire and away from said catheter shaft.

39. The catheter of claim 34, further comprising second guidewire removing means provided in said guidewire connector to permit a guidewire to be removed laterally from said access channel and from said first guidewire removing means.

40. The catheter of claim 39, wherein said second guidewire removing means comprises a portion of said guidewire connector that is removable laterally away from said guidewire connector.

41. A method for using a vascular catheter, comprising the steps of:

inserting the catheter of claim 26 into a patient over the guidewire;

removing said guidewire and said stylet; and inserting said guidewire through the proximal opening of the guidewire lumen and out of the distal opening into a position in the vasculature of the patient.

42. The method of claim 41, further comprising the steps of:

holding said guidewire in said position in said patient while removing said catheter from said patient such that said guidewire passes laterally through said guidewire removing means until said catheter has been removed from said patient; and reinserting a catheter over said guidewire into said patient.

43. The method of claim 42, wherein said reinserted catheter and said guidewire together comprise the catheter of claim 34.

44. An angioplasty catheter for use in an animal body with a guidewire, comprising:

a catheter shaft having a proximal end and a distal end and having at least two lumens extending therethrough; and a "Y" connector surrounding at least a portion of the proximal end of the catheter shaft and having at least two arms, one arm providing an access channel into one of said lumens and another arm providing an access channel into another of said lumens, wherein said "Y" connector has at least two segments joined together in a separable manner along a longitudinal line that runs generally in the direction of one of said access channels so that upon separation of the segments, said "Y" connector no longer fully surrounds at least one of said access channels in said portion of said proximal end of said catheter shaft.

* * * * *